(12) United States Patent
Purdy

(10) Patent No.: US 7,787,954 B2
(45) Date of Patent: Aug. 31, 2010

(54) METHODS AND APPARATUSES FOR NAVIGATING THE SUBARACNHNOID SPACE

(75) Inventor: Phillip D. Purdy, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 8 days.

(21) Appl. No.: 12/323,204

(22) Filed: Nov. 25, 2008

(65) Prior Publication Data

US 2009/0076357 A1 Mar. 19, 2009

Related U.S. Application Data

(63) Continuation of application No. 09/905,670, filed on Jul. 13, 2001, now Pat. No. 7,455,666.

(51) Int. Cl.
*A61N 1/05* (2006.01)
(52) U.S. Cl. ............... 607/45; 607/2; 607/3; 607/115; 607/116; 607/117; 607/118; 600/378; 600/347
(58) Field of Classification Search ............... 607/2–3, 607/45, 115–118; 600/544, 347, 378
See application file for complete search history.

(56) References Cited

U.S. PATENT DOCUMENTS

| 3,782,388 A | 1/1974 | Page ........................... 604/180 |
| 4,619,643 A | 10/1986 | Bai ............................. 604/43 |
| 4,808,157 A | 2/1989 | Coombs ....................... 604/44 |
| 4,838,878 A | 6/1989 | Kalt et al. .................... 604/180 |
| 4,904,237 A | 2/1990 | Janese ......................... 604/28 |
| 4,911,163 A | 3/1990 | Fina ............................ 606/127 |
| 4,950,232 A | 8/1990 | Ruzicka et al. ................ 604/43 |
| 4,973,305 A | 11/1990 | Goltzer ........................ 604/509 |

(Continued)

FOREIGN PATENT DOCUMENTS

DE 37 26 453 2/1989

(Continued)

OTHER PUBLICATIONS

"Back Break," Article from *Forbes Magazine*, 123-124, Aug. 12, 2002.

(Continued)

*Primary Examiner*—Carl H Layno
*Assistant Examiner*—Paula J Stice
(74) *Attorney, Agent, or Firm*—Fulbright & Jaworski L.L.P.

(57) ABSTRACT

A method of navigating a spinal subarachnoid space in a living being includes percutaneously introducing a device into the spinal subarachnoid space at an entry location. The device has a first passageway that is sized to slidably receive, and work with, at least a guidewire. The device can be a catheter or a sheath. The method can also include advancing the device within the spinal subarachnoid space at least more than 10 centimeters from the entry location. Alternatively, the method can include advancing the device within the spinal subarachnoid space to facilitate intracranial access with a second device introduced through the first passageway. Also disclosed is a device suited for attachment to a patient's skin, such as a sheath, that includes an elongated member, a skin-attachment apparatus having a flexible skin-attachment flap, and a valve apparatus.

20 Claims, 10 Drawing Sheets

U.S. PATENT DOCUMENTS

| | | | | |
|---|---|---|---|---|
| 5,085,631 | A | 2/1992 | Leighton | 604/28 |
| 5,098,393 | A | 3/1992 | Amplatz et al. | 604/167.03 |
| 5,160,323 | A | 11/1992 | Andrew | 604/158 |
| 5,256,146 | A | 10/1993 | Ensminger et al. | 604/104 |
| 5,297,564 | A | 3/1994 | Love | 128/898 |
| 5,378,241 | A | 1/1995 | Haindl | 604/170.03 |
| 5,385,152 | A | 1/1995 | Abele et al. | 600/585 |
| 5,397,305 | A | 3/1995 | Kawula et al. | 604/96.01 |
| 5,423,760 | A | 6/1995 | Yoon | 604/164.11 |
| 5,423,849 | A | 6/1995 | Engelson et al. | 606/191 |
| 5,445,625 | A | 8/1995 | Voda | 604/532 |
| 5,449,343 | A | 9/1995 | Samson et al. | 604/95.01 |
| 5,470,318 | A | 11/1995 | Griffith, III et al. | 604/161 |
| 5,478,331 | A | 12/1995 | Heflin et al. | 604/283 |
| 5,487,739 | A | 1/1996 | Aebisher et al. | 604/890.1 |
| 5,520,647 | A | 5/1996 | Solar | 604/102.02 |
| 5,542,936 | A | 8/1996 | Razi | 604/264 |
| 5,613,950 | A | 3/1997 | Yoon | 604/105 |
| 5,630,802 | A | 5/1997 | Moellmann et al. | 604/164.01 |
| 5,704,915 | A | 1/1998 | Melsky et al. | 604/175 |
| 5,731,284 | A | 3/1998 | Williams | 614/8 |
| 5,738,650 | A | 4/1998 | Gregg | 604/506 |
| 5,810,869 | A | 9/1998 | Kaplan et al. | 606/194 |
| 5,814,016 | A | 9/1998 | Valley et al. | 604/96.01 |
| 5,830,188 | A | 11/1998 | Abouleish | 604/158 |
| 5,833,632 | A | 11/1998 | Jacobsen et al. | 600/585 |
| 5,846,226 | A | 12/1998 | Urmey | 604/158 |
| 5,908,385 | A | 6/1999 | Chechelski et al. | 600/374 |
| 5,928,155 | A | 7/1999 | Eggers et al. | 600/526 |
| 5,928,260 | A | 7/1999 | Chin et al. | 606/200 |
| 5,931,810 | A | 8/1999 | Grabek | 604/506 |
| 5,935,122 | A | 8/1999 | Fourkas et al. | 604/523 |
| 5,951,520 | A | 9/1999 | Burzynski et al. | 604/170.01 |
| 5,980,480 | A | 11/1999 | Rubenstein et al. | 604/9 |
| 5,980,484 | A | 11/1999 | Ressemann et al. | 604/164.13 |
| 6,004,262 | A | 12/1999 | Putz et al. | 600/114 |
| 6,004,295 | A | 12/1999 | Langer et al. | 604/164.01 |
| 6,026,316 | A | 2/2000 | Kucharczyk et al. | 600/420 |
| 6,036,654 | A | 3/2000 | Quinn et al. | 600/526 |
| 6,061,587 | A | 5/2000 | Kucharczyk et al. | 600/411 |
| 6,080,140 | A | 6/2000 | Swaminathan et al. | 604/500 |
| 6,090,072 | A | 7/2000 | Kratoska et al. | 604/164.01 |
| 6,120,499 | A | 9/2000 | Dickens et al. | 606/41 |
| 6,129,713 | A | 10/2000 | Mangosong et al. | 604/264 |
| 6,146,354 | A | 11/2000 | Beil | 604/28 |
| 6,162,170 | A | 12/2000 | Foley et al. | 600/114 |
| 6,183,443 | B1 | 2/2001 | Kratoska et al. | 604/164.03 |
| 6,190,349 | B1 | 2/2001 | Ash et al. | 604/43 |
| 6,200,336 | B1 | 3/2001 | Pavcnik et al. | 623/1.15 |
| 6,214,029 | B1 | 4/2001 | Thill et al. | 606/213 |
| 6,233,488 | B1 | 5/2001 | Hess | 607/58 |
| 6,251,115 | B1 | 6/2001 | Williams et al. | 606/108 |
| 6,272,370 | B1 | 8/2001 | Gillies et al. | 600/411 |
| 6,319,241 | B1 | 11/2001 | King et al. | 604/502 |
| 6,328,694 | B1 | 12/2001 | Michaeli | 600/438 |
| 6,330,466 | B1 | 12/2001 | Hofmann et al. | 600/378 |
| 6,352,530 | B1 | 3/2002 | Mangosong | 604/506 |
| 6,379,331 | B2 | 4/2002 | Barbut et al. | 604/113 |
| 6,436,091 | B1 | 8/2002 | Harper et al. | 604/892.1 |
| 6,699,269 | B2 | 3/2004 | Khanna | 607/105 |
| 6,758,832 | B2 | 7/2004 | Barbut et al. | 604/113 |
| 6,761,715 | B2 | 7/2004 | Carroll | 606/21 |
| 7,286,879 | B2 * | 10/2007 | Wallace | 607/45 |
| 2004/0147433 | A1 | 7/2004 | Keep et al. | 514/11 |

FOREIGN PATENT DOCUMENTS

| | | |
|---|---|---|
| EP | 0 454 264 | 10/1991 |
| EP | 1 062 959 | 11/2004 |
| WO | WO 97/44082 | 11/1997 |
| WO | WO 98/38953 | 9/1998 |
| WO | WO 98/57603 | 12/1998 |
| WO | WO 99/20334 | 4/1999 |
| WO | WO 00/51669 | 9/2000 |
| WO | WO 01/54766 | 8/2001 |
| WO | WO 02/068036 | 9/2002 |

OTHER PUBLICATIONS

"Keeping it Cool," Article from *Health Communities, United Hospital*, 11:1, 8, Winter 2003.

Amar et al., "Microcatheterization of the cervical epidural space via lumbar puncture: Technical note," *Neurosurgery*, 48(5):1183-1187, 2001. Article from the Neurosurgery website at: http://www.neurosurgery-online.com, Oct. 23, 2001.

Blomberg, "A method for epiduroscopy and spinaloscopy. Presentation of preliminary results," *Acta Anaesthesiol. Scand.*, 29(1):113-116, 1985.

Blomberg, "Fibrous structures in the subarachnoid space: a study with spinaloscopy in autopsy subjects," *Anesth. Analg.*, 80(5):875-879, 1995.

Delhaas, "Extradural and subarachnoid catheterization using the Seldinger technique," *Br. J. Anaesth.*, 76(1):149-150, 1996.

Eguchi et al., "Endoscopy of spinal cord and posterior fossa by a lumbar percutaneous approach: endoscopic anatomy in cadavers," *Minim. Invasive Neurosurg.* 42(2):74-78, 1999.

Eguchi et al., "Endoscopy of the spinal cord: cadaveric study and clinical experience," *Minim. Invasive Neurosurg.*, 42(3):164-151, 1999.

Document depicting a prototype stent, sent to application on Jul. 13, 2001.

Fries and Reisch, "Biportal Neuroendoscopic Microsurgical Approaches to the Subarachnoid Cisterns. A Cadaver Study," *Minim. Invas. Neurosurg.*, 39:99-104, 1996.

Hamada et al., "Microcatheter intrathecal urokinase infusion into cisterna magna for prevention of cerebral vasospasm," *Stroke*, 31:2141-2148, 2000.

Karakhan et al., "Operative spinal endoscopy: stereotopography and surgical possibilities," *Acta. Neurochir. Suppl.*, 61:108-114, 1994.

Karakhan, "Use of intracranial endoscopy in morphologic studies," *Arkh. Anat. Gistol. Embriol.*, 98(1):75-82, 1990. Russian.

Miyamoto et al., "The development of spinal endocope using a flexible optic fiber," *No. To. Shinkei*, 41(12):1233-1238, 1989. Abstract on p. 1238.

Office Communication, issued in U.S. Appl. No. 09/905,670, dated May 4, 2005.

Response to May 4, 2005 Office Communication, submitted Jun. 6, 2005.

Office Communication, issued in U.S. Appl. No. 09/905,670, dated Sep. 22, 2005.

Response to Sep. 22, 2005 Office Communication, submitted Dec. 27, 2005.

Office Communication, issued in U.S. Appl. No. 09/905,670, dated Apr. 20, 2006.

Response to Apr. 20, 2006 Office Communication, submitted Sep. 1, 2006.

Pre-Appeal Brief Request for Review, U.S. Appl. No. 09/905,670, submitted May 12, 2006.

Office Communication, Notice of Panel Decision from Pre-Appeal Brief Review, issued in U.S. Appl. No. 09/905,670, dated Jul. 24, 2006.

Office Communication, Notice of Panel Decision from Pre-Appeal Brief Review, issued in U.S. Appl. No. 09/905,670, dated Aug. 3, 2006.

Office Communication, Notice of Non-Compliant Amendment, issued in U.S. Appl. No. 09/905,670 dated Sep. 7, 2006.

Response to Sep. 7, 2006 Office Communication, submitted Oct. 2, 2006.

Office Communication, issued in U.S. Appl. No. 09/905,670, dated Nov. 7, 2006.

Response to Nov. 7, 2006 Office Communication, submitted Mar. 8, 2007.

Office Communication, issued in U.S. Appl. No. 09/905,670, dated Mar. 26, 2007.

Response to Mar. 26, 2007 Office Communication, submitted Jun. 19, 2007.
Office Communication, issued in U.S. Appl. No. 09/905,670, dated Aug. 27, 2007.
Response to Aug. 27, 2007 Office Communication, submitted Nov. 19, 2007.
Office Communication, issued in U.S. Appl. No. 09/905,670, dated Dec. 10, 2007.
Response to Dec. 10, 2007 Office Communication, submitted Jan. 23, 2008.
Office Communication, issued in U.S. Appl. No. 09/905,670, dated Mar. 5, 2008.
Response to Mar. 5, 2008 Office Communication, submitted Jun. 5, 2008.

Stefanov et al., "A new method for transcutaneous coaxial neuroendoscopy," *Anat. Embryol.*, 194(4):319-326, 1996.
Suzukawa et al., "Percutaneous fiberoptic spinal laser endoscopy," *J. Clin Laser Med Surg.*, 8(6):27-30, 1990.
Tanaka et al., "Endoscopic treatment of symptomatic spinal subarachnoid cysts," *AJR Am. J. Roentgenol.* 169(6):1719-1720, 1997.
Uchiyama et al., "Ultrafine Flexible Spinal Endoscope (Myeloscope) and Discovery of an Unreported Subarachnoid Lesion," *Spine*, 23(21):2358-2362, 1998.
Vinas et al., "Microanatomical basis for the third ventriculostomy," *Minim. Invasive Neurosug.* 39(4):116-121, 1996.

\* cited by examiner

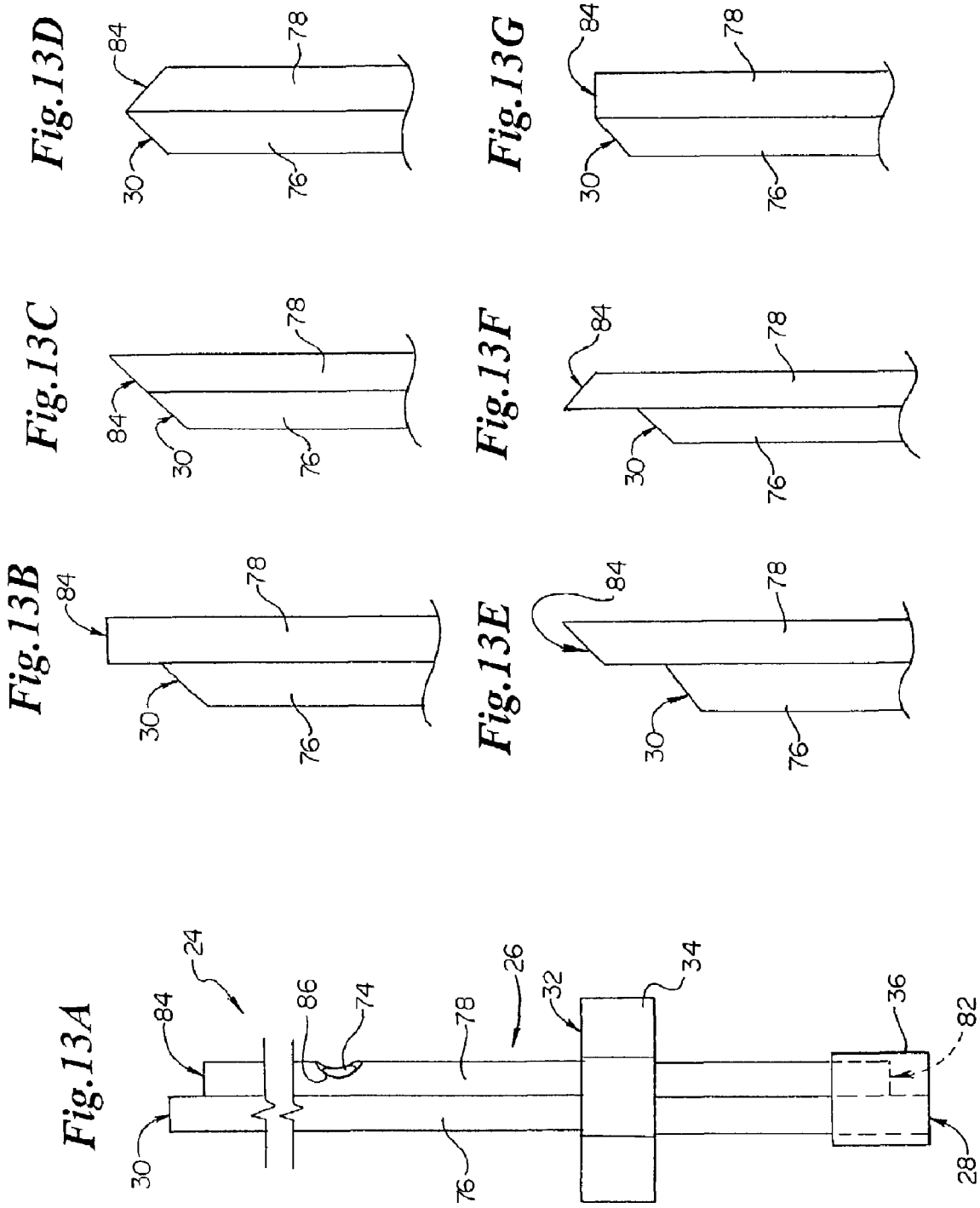

METHODS AND APPARATUSES FOR NAVIGATING THE SUBARACNHNOID SPACE

CROSS REFERENCE TO RELATED APPLICATION

This patent application is a continuation of Ser. No. 09/905,670, filed on Jul. 13, 2001, now U.S. Pat. No. 7,455,666, which is incorporated by reference.

BACKGROUND OF THE INVENTION

1. Field of the Invention

The present invention relates generally to surgical methods and medical devices. More particularly, it concerns methods and apparatuses useful in navigating the subarachnoid space, including the spinal and the intracranial subarachnoid spaces. It also concerns medical devices, such as sheaths, that are suited for attachment to the skin.

2. Description of Related Art

During the 20$^{th}$ century, brain neurosurgery has advanced via the introduction of microsurgical techniques, the development of new tools such as aneurysm clips, and the description of new operative approaches. Surgeons have developed elegant mechanisms to remove parts of the bones making up the skull (craniotomy) and operate on structures deep within the brain while attempting to minimize complications relating to the approach. [See, for example, Fries et. al., 1996.] Furthermore, the surgical approach to the intracranial and spinal subarachnoid space has historically consisted of the skin incision, dissection to either the cranium or spinal bony covering, removal of some bone, and dissection through the meninges to gain access to the neurological structures. While imaging modalities became integrated into diagnostic evaluations, only at the end of the last century were significant attempts made to integrate computed tomography, angiography, and most recently magnetic resonance (MR) scanning into the actual surgical procedures.

Unfortunately, craniotomy has limited the applicability of such imaging modalities because the surgeon cannot simultaneously stand at the patient's head and conveniently operate on the brain via craniotomy, maintain sterility, and scan the brain using a large scanning apparatus that requires the patient to be held within it. There are theoretical limits to the ability to conveniently perform such surgery using currently-available imaging devices due to a conflict between the means of acquiring images and the means of operating on the brain. Furthermore, in conventional neurosurgery, while the brain surface is readily available underlying a craniotomy, the approach to deeper structures is progressively more invasive in terms of retraction injury (i.e., the brain is often retracted after the craniotomy to facilitate access to different areas in and around the brain) or even the need to remove brain tissue to gain access.

During the last 20 years, the development of endovascular neurosurgery has resulted in the creation of specialized devices for application within arteries. These devices include not only catheters and guidewires, but also embolic materials that can be introduced via catheters, thereby enabling the enhancement of some procedures that are performed via craniotomy following embolization, and thereby eliminating the need for craniotomy altogether in other cases. However, these techniques have heretofore been limited to the intravascular space (i.e., the space within blood vessels) because that was seen as the only available route of access for catheterization of the intracranial contents.

Extravascular access to locations within the head for the purpose of facilitating the kinds of procedures heretofore performed following a craniotomy has not been reported to the inventor's knowledge. The subarachnoid space, which is a compartment that contains the body of the spinal cord and cerebrospinal fluid (CSF)—a fluid that fills and surrounds the ventricles (cavities) of the brain and the spinal cord, and acts as a lubricant and a mechanical barrier against shock—is one such extravascular route.

Some authors have described experimental data using endoscopy in the subarachnoid space. An endoscope is a tube with a light and a lens on the end that can be used to view various regions within a body. One group from Sweden utilized a relatively large (4 millimeter) bronchoscope (a type of endoscope) to travel the length of the subarachnoid space to eventually visualize the contents of the posterior fossa, as well as gain access to the ventricular system. [Stefanov et. al., 1996.] These studies were performed in cadavers and involved dissection to the lumbar space and introduction of the bronchoscope from that location, using only endoscopic guidance. Applications in the clinical setting were not advocated.

A group from Japan utilized a smaller endoscope in cadavers to access only the subarachnoid space around the spinal cord and posterior fossa. [Eguchi et. al., 1999.] No attempt was made to access either the ventricles or the supratentorial cisterns. The endoscopes used also had no directional capability. Uchiyama et. al. (1998) used a "myeloscope" (a type of endoscope) that was sufficiently small (0.5-2 mm) to safely access the spinal subarachnoid space without injuring the spinal cord in a group of patients. Neither of these articles discusses catheterizing the subarachnoid space, whether for the purpose of facilitating intracranial access or otherwise. Furthermore, neither group attempted navigation of the subarachnoid space using catheters and guidewires or other means to more precisely control device placement or other instrument insertion.

Amar et. al. (2001) recently described a technique of catheterizing the spinal epidural space for the introduction of medication. However, that technique did not involve catheterization of the subarachnoid space, nor was it performed for the purpose of facilitating intracranial access. Other techniques of delivering anesthetics and other therapeutic agents to the subarachnoid space using catheters are described in U.S. Pat. Nos. 5,085,631 and 5,470,318.

The techniques disclosed in these patents do not involve advancing the catheter toward the head of the patient after the catheter is introduced into the subarachnoid space. Nor do they involve steps that facilitate intracranial access. Neither patent discloses using catheters for introducing other medical devices through the passageways in those catheters for the purpose of facilitating intracranial access.

The inventor is aware of other techniques for delivering medicaments to the subarachnoid space using a catheter. However, of these, none involved the use of catheters for the purpose of facilitating intracranial access. [See, for example, Delhaas, 1996.]

In addition, medical devices (e.g., sheaths) that are used with the foregoing techniques to facilitate the introduction of endoscopes and catheters into the subarachnoid space are not well-suited for use with imaging modalities such as MR scanning. Generally, once a sheath is in place within a patient, other devices such as endoscopes and catheters can be introduced into the patient through the passageway within the sheath. In other words, once the sheath is in place, one end of the sheath is located beneath the patient's skin while the other end sticks out of the patient's skin, thereby allowing the surgeon to introduce, for example, an endoscope or catheter into the patient through the sheath's passageway. The manipulations that cause these introductions to occur are carried out at the end of the sheath that is positioned outside of the patient. However, a traditional sheath is sized and configured such that it does not extend very far outside of a patient once it has been inserted into a desired location. As a result, the manipulations of other medical devices introduced through the sheath cannot feasibly take place while the patient is positioned within an MR scanner (which mainly consists of large magnets) because there simply is not enough of the sheath sticking out of the patient to work with. Furthermore, this same shortcoming would impede a surgeon's ability to use one or more robotic devices to assist in or completely perform these manipulations.

Based on the foregoing, new methods of facilitating intracranial access that do not involve the shortcomings of craniotomy, and that can be monitored or guided via various imaging modalities are needed. New methods of facilitating intracranial access via devices introduced through non-endoscopic devices are also needed. Furthermore, new medical devices useful for establishing access to areas such as the subarachnoid space, and that can be used with robotic instruments or while the patient is positioned within an MR scanner are needed.

SUMMARY OF THE INVENTION

The present invention addresses the shortcomings of the prior art by providing methods of navigating the subarachnoid space that does not involve the removal of bone. In addition, the present invention provides a medical device that is suited for attachment to the skin, and which enhances the flexibility afforded to the operating carrying out the present methods.

In one respect, the invention is a method of navigating a spinal subarachnoid space in a living being. The method includes percutaneously introducing a device into the spinal subarachnoid space at an entry location. The device has a first passageway sized to slidably receive, and work with, at least a guidewire. The method also includes advancing the device within the spinal subarachnoid space at least more than 10 centimeters from the entry location.

In one embodiment, method also includes removing a portion of the brain of the living being. The living being contains cerebrospinal fluid, and in another embodiment, the method also includes flushing at least some cerebrospinal fluid in order to remove blood from that cerebrospinal fluid. In another embodiment, the method also includes inducing hypothermia in at least some brain tissue. In another embodiment, the method also includes accessing at least one ventricle located within the head with a second device introduced through the first passageway of the device. In another embodiment, the method also includes draining at least one ventricle located within the head after accessing the ventricle.

In another embodiment, the device includes a second passageway sized to slidably receive, and work with, at least a guidewire. In another embodiment, the method also includes introducing an endoscope through the first passageway of the device. In another embodiment, the device includes a first sub-elongated member that has the first passageway, and a second sub-elongated member coupled to the first sub-elongated member, and the second sub-elongated member has the second passageway. In another embodiment, the device also includes a braiding material wrapped around the first and second sub-elongated members.

In another embodiment, a cross section taken along the device has a shape that is non-circular. In another embodiment, the method also includes altering the temperature of at least some brain tissue using a pumping apparatus. In another embodiment, the method also includes delivering medication to an intracranial subarachnoid space. In another embodiment, the device includes a wall to which an electroencephalography electrode is attached. In another embodiment, the device includes a wall to which a sensor useful for monitoring a biochemical property is attached, and the method also includes monitoring either pH, glucose concentration, oxygen tension, carbon dioxide concentration, or sodium concentration using the sensor. In another embodiment, the device includes a wall to which a thermal sensor useful for monitoring temperature is attached, and the method also includes monitoring temperature using the thermal sensor.

In another embodiment, the method also includes introducing an apparatus through the first passageway of the device; and applying electric current, heat, or cryothermal stimulation to a tissue within the living being using the apparatus. In another embodiment, the method also includes introducing a radioactive pellet through the first passageway of the device; and placing the radioactive pellet within the living being in order to irradiate a tumor. In another embodiment, the method also includes introducing a detector through the first passageway of the device; and placing the detector within the living being. In another embodiment, the method also includes monitoring a physiologic or biochemical property using the detector.

In another embodiment, the method also includes introducing a penetration apparatus through the first passageway of the device, the penetration apparatus including an outer sleeve element and an inner puncture element, the outer sleeve element and the inner puncture element being slidably coupled together; and puncturing the pia mater using the penetration apparatus. In another embodiment, the method also includes creating a lesion in the brain of the living being. In another embodiment, the advancing step of the method is achieved via a robotic device. In another embodiment, the method also includes monitoring the position of the device for a period of time using magnetic resonance imaging, fluoroscopy, endoscopy, computed tomography, thermal imaging, sonography, or any combination of these. In another embodiment, the method also includes introducing an electrode through the first passageway of the device; and placing the electrode within the living being. In another embodiment, the electrode is an electroencephalography electrode and the placing includes placing the electroencephalography electrode proximate brain tissue. In another embodiment, the method also includes introducing material through the first passageway of the device; and placing the material proximate a cranial nerve to assist in treating a neurologic condition. In another embodiment, the method also includes introducing genetic material through the first passageway of the device; and placing the genetic material within the living being to assist in treating a neurologic condition.

In another respect, the invention is a method of navigating a spinal subarachnoid space in a living being. The method includes percutaneously introducing a device into the spinal subarachnoid space. The device has a first passageway sized to slidably receive, and work with, at least a guidewire. The method also includes advancing the device within the spinal subarachnoid space to facilitate intracranial access with a second device introduced through the first passageway.

In one embodiment, the method also includes removing a portion of the brain of the living being. The living being contains cerebrospinal fluid, and in another embodiment, the method also includes flushing at least some cerebrospinal fluid in order to remove blood from that cerebrospinal fluid. In another embodiment, the method also includes inducing hypothermia in at least some brain tissue. In another embodiment, the method also includes accessing at least one ventricle located within the head with a second device introduced through the first passageway of the device. In another embodiment, the device includes a second passageway sized to slidably receive, and work with, at least a guidewire. In another embodiment, the device includes a first sub-elongated member that has the first passageway, and a second sub-elongated member coupled to the first sub-elongated member, and the second sub-elongated member has the second passageway. In another embodiment, the device includes a wall to which a sensor useful for monitoring a biochemical property is attached, and the method also includes monitoring either pH, glucose concentration, oxygen tension, carbon dioxide concentration, or sodium concentration using the sensor.

In another embodiment, the method also includes introducing an apparatus through the first passageway of the device; and applying electric current, heat, or cryothermal stimulation to a tissue within the living being using the apparatus. In another embodiment, the method also includes introducing a radioactive pellet through the first passageway of the device; and placing the radioactive pellet within the living being in order to irradiate a tumor. In another embodiment, the method also includes introducing a detector through the first passageway of the device; and placing the detector within the living being. In another embodiment, the method also includes monitoring a physiologic or biochemical property using the detector. In another embodiment, the advancing step of the method is achieved via a robotic device. In another embodiment, the method also includes monitoring the position of the device for a period of time using magnetic resonance imaging, fluoroscopy, endoscopy, computed tomography, thermal imaging, sonography, or any combination of these.

In yet another embodiment, the method also includes introducing an electrode through the first passageway of the device; and placing the electrode within the living being. In another embodiment, the electrode is an electroencephalography electrode and the placing includes placing the electroencephalography electrode proximate brain tissue.

In another respect, the invention is a method of navigating a spinal subarachnoid space within a living being. The method includes introducing a non-endoscopic device into the spinal subarachnoid space. The non-endoscopic device has a passageway. The method also includes advancing the non-endoscopic device within the spinal subarachnoid space and toward the head of the living being to facilitate intracranial access with a second device introduced through the passageway; and monitoring the position of the non-endoscopic device for a period of time using an imaging modality other than an endoscope. In this document (including the claims), a "non-endoscopic device" is one that is not an endoscope. In this document (including the claims), an "endoscope" is a device to which a lens has been directly attached (usually at a tip of the device). A device such as one of the catheters or sheaths discussed below that has a passageway through which an endoscope is passed and with which an endoscope is used does not become an endoscope as a result.

In another respect, the invention is a medical device suited for attachment to a patient's skin. The medical device includes a member that has two ends and a first passageway sized to slidably receive, and work with, at least a guidewire; and a skin-attachment apparatus that is configured to be coupled to the member at a coupling location that is between the two ends. The skin-attachment apparatus has a flexible skin-attachment flap configured for attachment to the skin. The medical device also includes a valve apparatus that is configured to be coupled to one end of the member. The valve apparatus and the skin-attachment apparatus define a flexible member portion between them when both are coupled to the member.

In one embodiment, the coupling location is variable during a procedure. In one embodiment, the medical device also includes a second skin-attachment apparatus that is configured to be coupled to the member at a second coupling location that is spaced apart from the coupling location. In one embodiment, the flexible member portion has a length of at least 2 centimeters. In one embodiment, a cross section taken along the member has a shape that is non-circular. In one embodiment, the member has a second passageway. In one embodiment, the member includes a first sub-elongated member that has the first passageway, and the medical device also includes a second sub-elongated member coupled to the first sub-elongated member, and the second sub-elongated member has the second passageway.

In another embodiment, the member is bendable, and is configured to retain a shape after being bent. In another embodiment, the valve apparatus is configured for use with a robotic device. In another embodiment, the member has a length, and a stiffness that varies along the length. In another embodiment, the two ends of the member are first and second ends; the valve apparatus is configured to be coupled to the first end; the member has a distal portion near the second end; and the distal portion includes a wall that has an electroencephalography electrode therein. In another embodiment, the two ends of the member are first and second ends; the valve apparatus is configured to be coupled to the first end; the member has a distal portion near the second end; and the distal portion includes a wall that has a sensor useful for monitoring a biochemical property. In another embodiment, the biochemical property is pH, glucose concentration, oxygen tension, carbon dioxide concentration, or sodium concentration. In another embodiment, the two ends of the member are first and second ends; the valve apparatus is configured to be coupled to the first end; the member has a distal portion near the second end; and the distal portion includes a wall that has a thermal sensor useful for monitoring temperature.

In yet another embodiment, the medical device also includes a flush line coupled to the valve apparatus. In another embodiment, the flexible skin-attachment flap includes padding material. In another embodiment, the valve apparatus includes a hub configured for attachment to other medical devices.

In another respect, the invention is a sheath suited for attachment to a patient's skin. The sheath includes a member that has a first end, a second end, and a first passageway sized to slidably receive, and work with, at least a guidewire. The sheath also has a skin-attachment apparatus that is configured to be coupled to the non-rigid member at a coupling location that is between the first and second ends, but at least 2 centimeters from the first end. The skin-attachment apparatus has a flexible, padded skin-attachment flap configured for attachment to the skin. The medical device also includes a valve apparatus that is configured to be coupled to the first end of the member. The valve apparatus and the skin-attachment apparatus define a flexible member portion between them when both are coupled to the member. The coupling location may be varied either prior to or after attachment of the sheath to the skin.

BRIEF DESCRIPTION OF THE DRAWINGS

The following drawings form part of the present specification and are included to further demonstrate certain aspects of the present methods and apparatuses. The present methods and apparatuses may be better understood by reference to one or more of these drawings in combination with the description of illustrative embodiments presented herein. These drawings illustrate by way of example and not limitation, and they use like references to indicate similar elements.

FIG. 13A illustrates sub-elongated members of different lengths.

FIGS. 13B-H are partial side views illustrating different embodiments of ends of two coupled sub-elongated members.

DESCRIPTION OF ILLUSTRATIVE EMBODIMENTS

As a preliminary matter, it should be noted that in this document (including the claims), the terms "comprise" (and any form thereof, such as "comprises" and "comprising"), "have" (and any form thereof, such as "has" and "having"), and "include" (and any form thereof, such as "includes" and "including") are open-ended transitional terms. Thus, a thing that "comprises," "has," or "includes" one or more elements possesses those one or more elements, but is not limited to only possessing those one or more elements. For example, a device "having a first passageway sized to slidably receive, and work with, at least a guidewire" is a device that has, but is not limited to only having, the described first passageway. In other words, the device possesses the first passageway, but is not excluded from possessing additional passageways or other elements that are not listed.

The present methods involve navigating the subarachnoid space, including the spinal subarachnoid space. In some embodiments, the intracranial subarachnoid space is also navigated. The present methods facilitate intracranial access via the subarachnoid space. For example, using the present methods, a first device may be introduced into the subarachnoid space to facilitate intracranial access with another device introduced through one or more passageways located within the first device. In this document (including the claims), "intracranial access" means access to the space within the head that is above the foramen magnum. In addition, intracranial subarachnoid space is the subarachnoid space located above the foramen magnum, and the spinal subarachnoid space is the subarachnoid space located below the foramen magnum, though the spaces are contiguous without a physical barrier between them. In this document (including the claims), a step that involves moving one device "to facilitate intracranial access" with another device introduced through the first device is a step that is taken with the intention of making intracranial access with the second device possible.

The present minimally-invasive methods offer new routes of access for both brain and spine surgery that involve no craniotomy or bone removal. Advantageously, the present methods can be performed with the operator standing remote from the patient's head. The route of access is a standard puncture of the spinal subarachnoid space, such as in the lumbar spine. Then, techniques conventionally used in intravascular procedures are applied in order to navigate the subarachnoid space, including the intracranial subarachnoid space in some cases. The present methods should have fewer problems with exposure of the brain to infectious agents and offer an opportunity for navigation of many structures without brain retraction or removal to achieve access.

Figure 1:
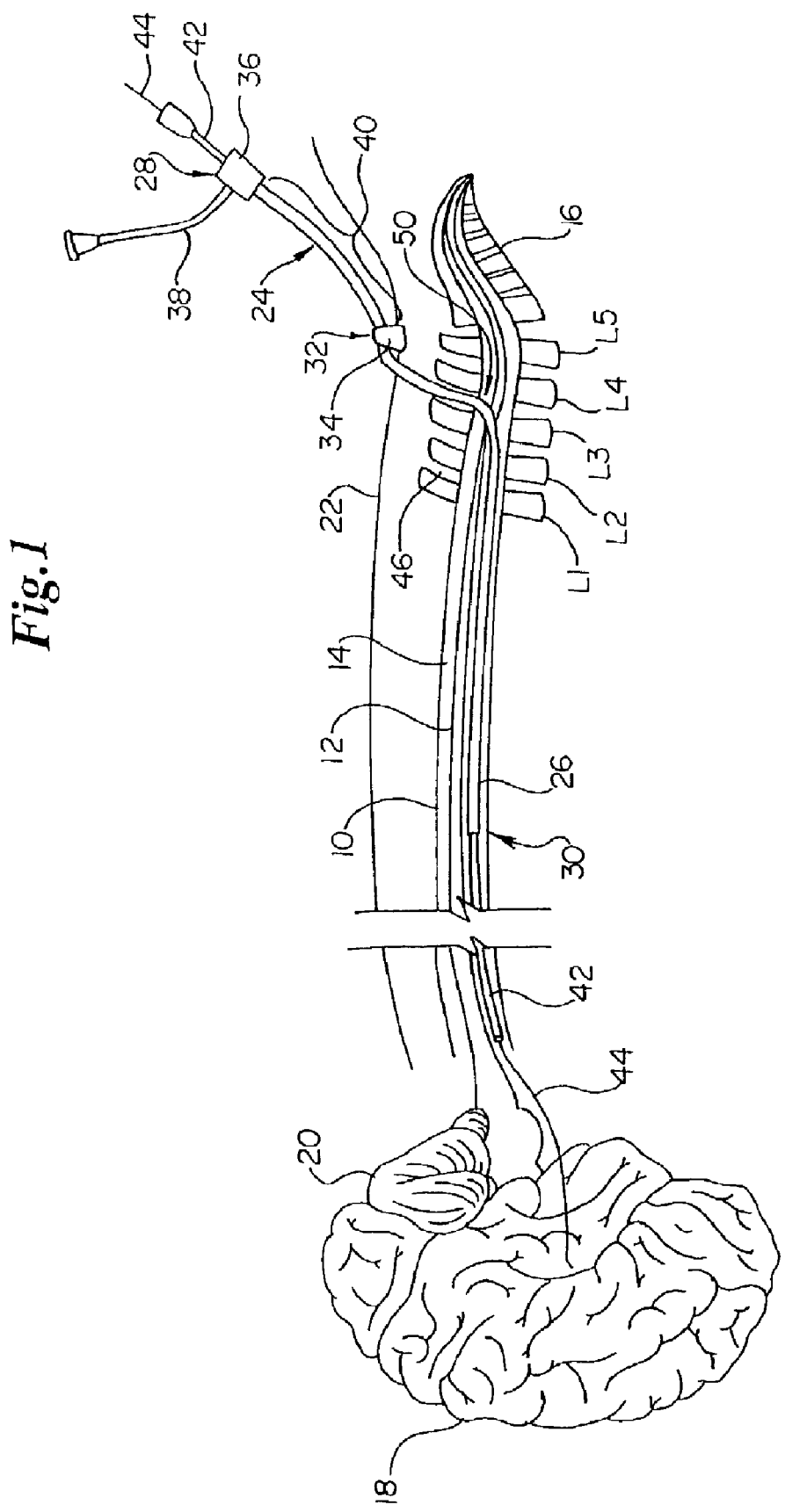
FIG. 1 illustrates selected areas of the central nervous system and medical devices introduced into the spinal subarachnoid space using the present methods.

Turning to the figures, FIG. 1 illustrates certain aspects of the central nervous system of a patient that have been navigated using the present techniques. Specifically, FIG. 1 illustrates dural membrane 10, spinal cord 12, subarachnoid space 14, lumbar vertebrae L1, L2, L3, L4, and L5, sacrum 16, and brain 18, including cerebellum 20. FIG. 1 also illustrates as sheath 24 a medical device suited for attachment to skin 22, which includes elongated member 26, first end 28, second end 30, skin-attachment apparatus 32, valve apparatus 36 coupled to first end 28, and flush line 38. As used in this document (including the claims), "elongated" simply means having a length. Skin-attachment apparatus 32 includes flexible skin-attachment flap 34 configured for attachment (and actually attached as shown) to skin 22. Further, skin-attachment apparatus 32 is configured to be coupled to elongated member 26 at a location along elongated member 26 described in this document (including the claims) as a "coupling location." FIG. 1 illustrates that skin-attachment apparatus 32 and valve apparatus 36, which are both coupled to elongated member 26, define flexible member portion 40 between them.

As shown in FIG. 1, elongated member 26 includes a first passageway that is sized to slidably receive, and work with, at least a guidewire. In this document (including the claims), a passageway that is "sized to slidably receive, and work with, at least a guidewire" means that the passageway is configured for use in normal operation with a medical device that can be the size of at least a guidewire. Thus, a passageway so sized is configured for use in normal operation with a guidewire, and may also be configured for use in normal operation with larger medical devices, including certain sheaths, catheters, and dilators. As shown in FIG. 1, another device having a first passageway that is sized to slidably receive, and operate with, at least a guidewire is illustrated as catheter 42, which has been percutaneously introduced into subarachnoid space 14 at entry location 50 through the first passageway of elongated member 26. Guidewire 44 is shown in FIG. 1 as having been percutaneously introduced into subarachnoid space 14 at entry location 50 through the first passageways of both catheter 42 and elongated member 26. As used in this document (including the claims), "introducing a device into the subarachnoid space" means causing the device to pass through the boundary that defines the spinal subarachnoid space. The boundary need not be physical, so the device does not need to be in contact with the subarachnoid space. Thus, and for example, passing a guidewire or a catheter through the passageway in a sheath that is positioned within the subarachnoid space amounts to introducing that guidewire or catheter into the subarachnoid space so long as that guidewire or catheter passes across the boundary that defines where the subarachnoid space begins. Furthermore, as used in this document (including the claims), "percutaneously introducing" a device means to introduce the device without first cutting away bone through, for example, craniotomy or drilling burr holes.

Prior to percutaneously introducing sheath 24 into subarachnoid space 14 at entry location 50, an operator may direct a guidewire through skin 22 and dural membrane 10 and into subarachnoid space 14, and more specifically the spinal subarachnoid space, in order to facilitate the introduction of sheath 24. This guidewire introduction may be achieved, for example, by directing a needle through the skin and the dural membrane between any of the lumbar vertebrae. The spaces between adjacent vertebrae are known as interspaces, such as the L1-2 interspace labeled as element 46.

While FIG. 1 illustrates introduction into the subarachnoid space (and specifically into the spinal subarachnoid space) in the lumbar region, entry locations may be made in other regions, including the thoracic and cervical regions of the spine. Thus, devices such as catheters, sheaths, and guidewires (including those illustrated in FIG. 1) may pass through the following interspaces: C1-2, C2-3, C3-4, C4-5, C5-6, C6-7 (i.e., the cervical interspaces), T1-2, T2-3, T3-4, T4-5, T5-6, T6-7, T7-8, T8-9, T9-10, T10-11, and T11-12 (i.e., the thoracic interspaces). With the needle in place, a guidewire may be introduced into the spinal subarachnoid space through a passageway (sometimes referred to as a "lumen") within the needle. The guidewire may then be directed superiorly and advanced within the spinal subarachnoid space and toward the patient's head to a desired location. The position of the guidewire within the patient, including within the various regions of the subarachnoid space, may be monitored using any suitable imaging modality, such as magnetic resonance imaging, fluoroscopy, endoscopy, computed tomography, thermal imaging, sonography, or any combination of these. Moreover, these imaging modalities can be used throughout a procedure to monitor the various positions of other medical devices, provided that the right conditions exist (such as sufficient radiopacity, etc.)

After introducing a guidewire, such as guidewire 44, into the subarachnoid space, the operator may dilate the tract created by the guidewire using one or more medical devices suited for that purpose, such as dilators. This may be done after removing the needle. Alternatively, a suitably structured sheath may be introduced over the guidewire for the same dilation purpose and also to facilitate intracranial access with a second device introduced through the passageway of the sheath. If an operator uses a dilator, a medical device such as sheath 24 may be passed over the dilator, and the dilator can then be removed through the passageway of the sheath.

Following sheath placement, techniques applied during procedures such as angiography may be used to navigate the subarachnoid space, including the spinal and intracranial subarachnoid spaces. In this regard, another guidewire may be introduced through the sheath and into the subarachnoid space with a tip that is directed either anteriorly or posteriorly in relation to the spinal cord. A medical device such as a catheter may then be introduced over the guidewire to facilitate intracranial access using a device introduced through the passageway of the catheter.

The navigation described above, including one or more of the steps for introducing the various medical devices into the subarachnoid space and advancing those devices within the subarachnoid space and, sometimes, toward the head of the patient, may be achieved in whole or in part using a robotic device. Furthermore, the representative applications of the present methods discussed below may be carried out in whole or in part using a robotic device. Potential advantages of using a robotic device in this fashion pertain, for example, to navigating through neural tissue. The pial membrane surrounding the brain forms a barrier to penetration, and once the membrane is punctured, there is essentially no resistance to navigation offered by cerebral tissue. Using a robotic device to assist with navigation of the cerebral tissue may be beneficial given the great extent to which the movements of a catheter or guidewire can be controlled using a robotic device and viewed using an imaging modality.

Figure 2A:
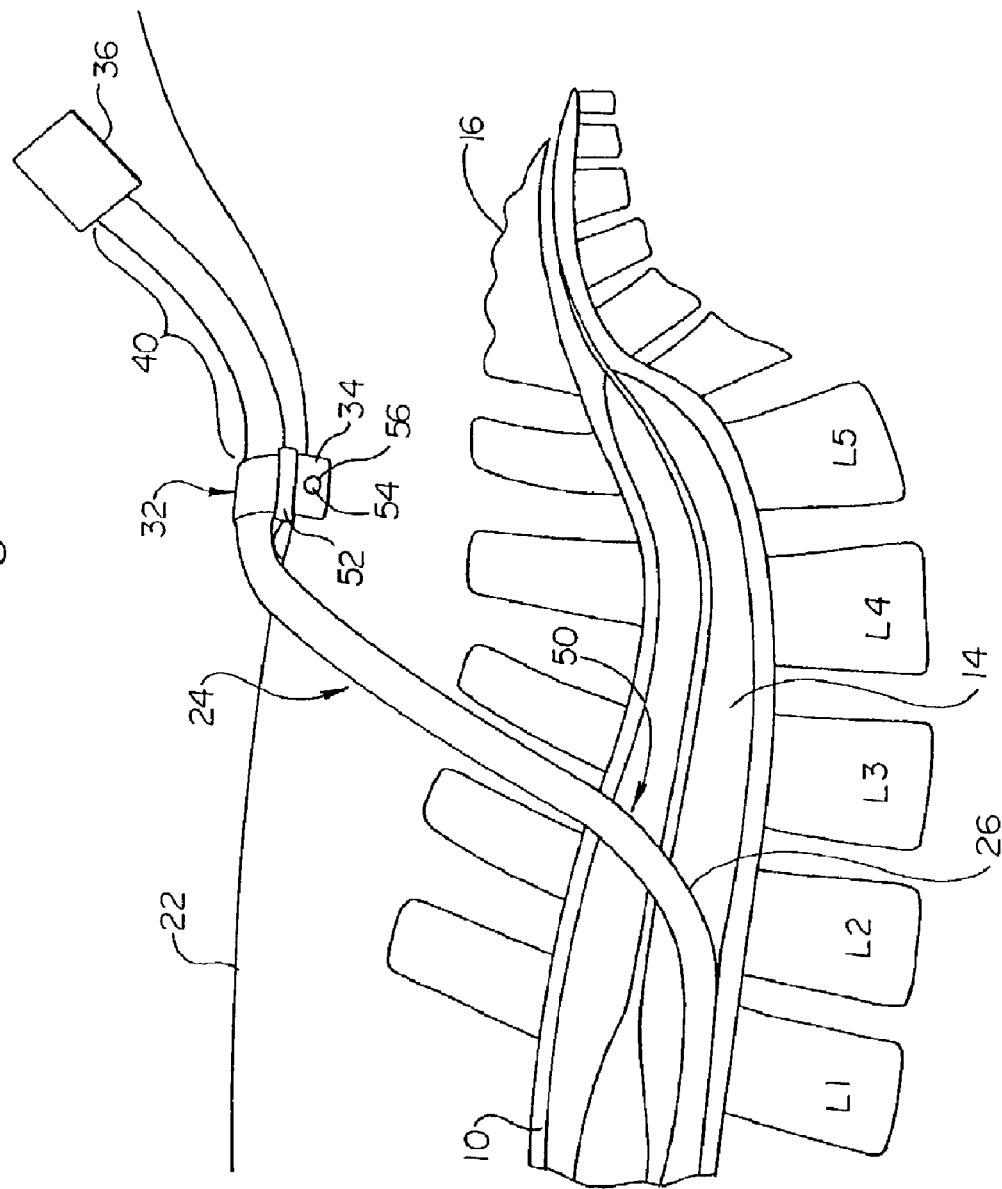
FIGS. 2A and 2B are enlarged versions of the lumbar region of the spine shown in FIG. 1, and illustrate a medical device suited for attachment to the skin that was placed using the present methods.

Turning next to FIG. 2A, an enlarged view of a small portion of the central nervous system is illustrated, and sheath 24 is shown positioned within the subarachnoid space 14. As shown in FIG. 2A, subarachnoid space 14 is the spinal subarachnoid space. The spinal subarachnoid space is located within the bony canal created by the vertebrae and is different than the intracranial subarachnoid space, which is located above the foramen magnum, as described above. As shown, sheath 24 was percutaneously introduced into the spinal subarachnoid space through dural membrane 10 at entry location 50, and subsequently advanced through the spinal subarachnoid space and toward the head of the patient to facilitate intracranial access by both catheter 24 and guidewire 44. Skin-attachment apparatus 32, which is configured to be coupled to and, in fact, is coupled to, elongated member 26 of sheath 24, is shown as being attached to skin 22 using sutures 54 (only one of which is shown) placed through openings 56 (only one of which is shown) in flexible skin-attachment flap 34. Securing mechanism 52 is shown in FIG. 2A as being used with skin-attachment apparatus 32 to secure the position of skin-attachment apparatus 32 along elongated member 26. Advantageously, the coupling location of skin-attachment apparatus 32 to elongated member 26 may vary, thereby increasing the versatility of sheath 24 by comparison to sheaths with fixed skin-attachment apparatuses. Furthermore, by spacing apart skin-attachment apparatus 32 from valve apparatus 36, flexible member portion 40 is defined between the two.

Flexible member portion 40 affords the operator many advantages because it gives him/her the ability to introduce devices through the one or more passageways of sheath 24 at a location that is remote (i.e., spaced apart) from both the location at which the sheath is attached to the skin and the location at which the sheath enters the skin. For example, some patient motion during the operation can be absorbed by flexible member portion 40. Also, because the length of flexible member portion may be adjusted, the operator can position him or herself remotely from the patient when performing the various steps of the present methods and while permitting the position of various instruments to be monitored via imaging modalities such as magnetic resonance imaging (MRI). Thus, having a suitable length, flexible member portion 40 will allow extension of elongated member 26 from the area of the patient that will be inaccessible during placement of the patient in an MR scanners.

The length of the present flexible member portions, and the distance between one of the present skin-attachment apparatuses and the first end of one of the present elongated members (which distance will differ from the length of the present flexible member portion based on the length of the valve apparatus in question) can be any distance suited to the particular operation, including 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, or more centimeters. Additional suitable distances include 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70 centimeters, or even more if the particular application warrants further removal of the operating physician from the insertion point in the skin. Furthermore, the length of flexible member portion 40 can be adjusted to suit the use of sheath 24 with a robotic device.

Figure 2B:
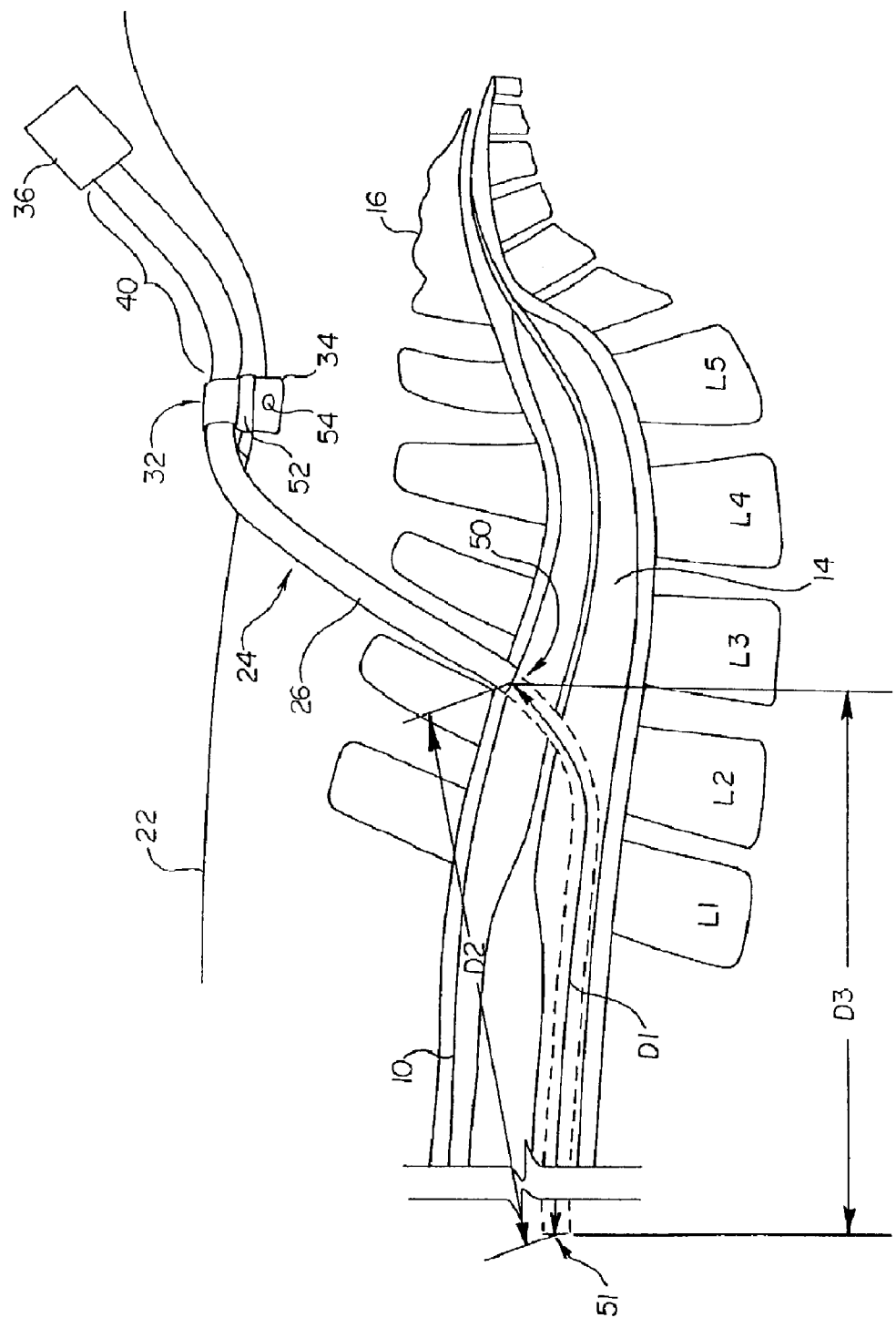

Moving to FIG. 2B, it shows a view similar to that depicted in FIG. 2A. Specifically, FIG. 2B illustrates sheath 24, which has been percutaneously introduced into subarachnoid space 14 (which, as shown, is spinal subarachnoid space) at entry location 50. From entry location 50, sheath 24 has been advanced (as shown by the dotted lines) a distance from that entry location to a second location 51. This distance is illustrated in FIG. 2B in terms of D1, which is the distance along the path taken by sheath 24. D1 can be determined by measuring the length of sheath 24 advanced beyond entry location 50. This distance is also illustrated in terms of D2, which is the straight-line distance between entry location 50 and second location 51. This distance is also illustrated as D3, which is the absolute distance toward the head that sheath 24 has been advanced between entry location 50 and second location 51. D3 can be determined by measuring the distance between a plane intersecting entry location 50 and oriented substantially laterally across the longitudinally-oriented patient and a plane intersecting second location 51 and oriented substantially laterally across the longitudinally-oriented patient.

In this document (including the claims), advancing a device a distance from an entry location means that the device is advanced a distance consistent with any of D1, D2, and D3. Thus, advancing a device at least greater than 10 centimeters from an entry location means that the device is advanced at least more than 10 centimeters (e.g., any distance that is greater than 10 centimeters, including 10.1 centimeters, etc.) according to the distance along the path taken by the device (i.e., D1), that the device is advanced at least more than 10 centimeters according to the straight-line distance from the entry location (i.e., D2), or that the device is advanced at least more than 10 centimeters according to the absolute distance in the direction of advancement from the entry location (i.e., D3). Suitable distances that the devices disclosed herein that have passageways sized to slidably receive, and operate with, at least a guidewire (such as sheath 24 and catheter 42) may be advanced within the spinal subarachnoid space from the entry location of the device consistent with the present methods include 1, 1.5, 2, 2.5, 3, 3.5, 4, 4.5, 5, 5.5, 6, 6.5, 7, 7.5, 8, 8.5, 9, 9.5, 10, 10.1, 10.2, 10.3, 10.4, 10.5, 10.6, 10.7, 10.8, 10.9, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, or more centimeters. Furthermore, distances that the devices disclosed herein that have passageways sized to slidably receive, and operate with, at least a guidewire (such as sheath 24 and catheter 42) may be advanced within the spinal subarachnoid space consistent with the present methods and that are greater than at least 10 centimeters from the entry location of the device include 10.1, 10.2, 10.3, 10.4, 10.5, 10.6, 10.7, 10.8, 10.9, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, or more centimeters. Further still and consistent with the present methods, the devices disclosed herein that have passageways sized to slidably receive, and operate with, at least a guidewire (such as sheath 24 and catheter 42) may be advanced within the spinal subarachnoid space distances from the entry locations of the devices greater than at least 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, or more centimeters.

Figure 3:
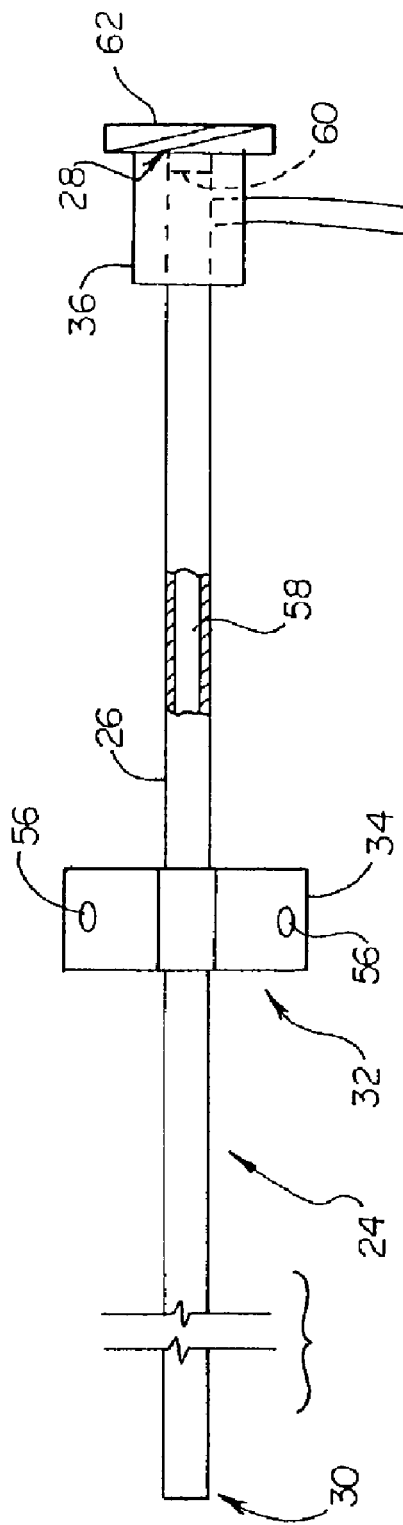
FIG. 3 is a top view of a medical device suited for attachment to the skin and illustrated as a sheath.

FIG. 3 illustrates a top view of sheath 24. As illustrated in a cut-away section of FIG. 3, elongated member 26 has a first passageway 58 that is sized to receive, and work with, at least a guidewire. Valve apparatus 36, which is configured to be coupled to and, in fact, is coupled to first end 28 of elongated member 26, provides a membrane 60 that extends across first passageway 58 in a way that allows other devices to be introduced through passageway 58 while preventing fluid from flowing out of sheath 24 through first end 28. Within this document (including the claims), a "valve apparatus" is any apparatus that, when coupled (either directly or indirectly) to elongated member 26, is capable of sealing one or more of the passageways (such as first passageway 58) of elongated member 26 against fluid trying to flow out through the particular passageway in a direction out of a patient. Although membrane 60 is shown as extending across first passageway 58 at a location within first passageway 58, those of skill in the art having the benefit of this disclosure will understand that membrane 60 could also be positioned outside of first passageway 58 and achieve the same function. For example, although not shown, those of skill in the art having the benefit of this disclosure will understand that membrane 60 could be formed as a rubber gasket situated between two elements that screw into each other and vary an opening within membrane 60, thereby providing an adjustable opening valve. Valve apparatus may be coupled to elongated member 26 using any suitable means, including a threaded connection, friction fit, interlocking parts, a clamp, glue, integral formation or other means of permanent attachment, or the like. In addition, valve apparatus 36 may be configured, as it is in FIG. 3, to allow for attachment of flush line 38. This may be accomplished in any conventional fashion, including through the use of a protrusion that is formed as part of valve apparatus 36 and extends away from it (not shown) to which a flush line may be coupled. Valve apparatus 36 may also be configured to allow for fluid communication between flush line 38 and first passageway 58. Alternatively, valve apparatus may also be configured to allow for fluid communication between flush line 38 and a passageway within elongated member 26 other than first passageway 58. Furthermore, valve apparatus 36 may be configured with hub 62 that is configured for attachment to other medical devices such as guidewires, sheaths, catheters, and introducers. The hub may, for example, take the form of a male or female Luer lock piece.

Although only one skin-attachment apparatus 32 is illustrated in the present figures, certain operations may benefit from the use of two or more such apparatuses. Accordingly, two, three, four, five, or more skin-attachment apparatuses configured to be coupled to elongated member 26 may be coupled to and used with elongated member 26. Each of these skin-attachment apparatuses may be coupled to elongated member 26 at coupling locations spaced apart from the ends of elongated member 26. One combination of skin-attachment apparatuses includes permanently attaching one to elongated member 26, and coupling another skin-attachment apparatus in between the permanently-attached skin-attachment apparatus and a valve apparatus coupled to the first end of the elongated member such that the coupling location of the second skin-attachment apparatus is variable. Furthermore, each skin-attachment apparatus may have a flexible skin-attachment flap that is configured for attachment to the skin of a patient. In this regard, while openings 56 are shown in flexible skin-attachment flap 34 for attaching the flexible skin-attachment flap to the skin of a patient, it will be understood that any suitable manner of configuring the flap for attachment to the skin may be used, including the use of a temperature sensitive adhesive, a repositionable adhesive, clips (such as small alligator clips), tape, glue, and the like.

Figure 4:
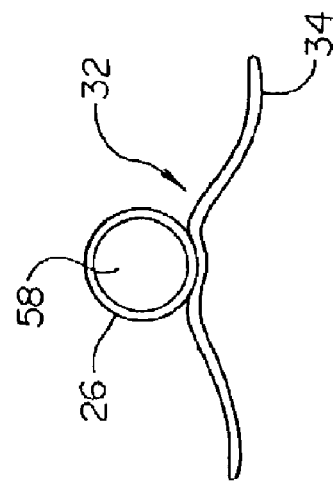

FIGS. 4-9 show different embodiments of skin-attachment apparatus 32. In FIG. 4, skin-attachment apparatus 32, which is configured to be coupled to elongated member 26 at a coupling location and which includes flexible skin-attachment flap 34, is coupled to elongated member 26 such that it is permanently attached to elongated member 26. This may be accomplished by securing flexible skin-attachment flap 34 to elongated member 26 through gluing, integral formation, or the like.

Figure 5:
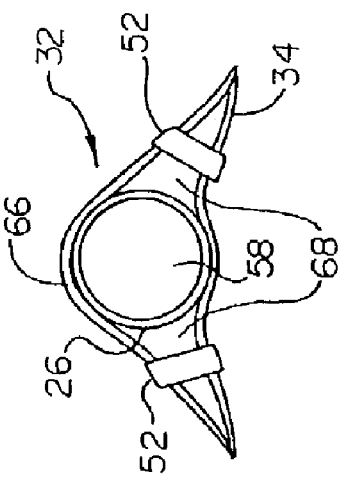
FIGS. 4-9 illustrate different embodiments of the skin-attachment apparatus that is coupled to the sheath shown in FIG. 3.

FIG. 5 shows skin-attachment apparatus 32 coupled to elongated member 26 in a way that permits the coupling location of skin-attachment apparatus to elongated member 26 to vary prior to or after attachment of skin-attachment apparatus to a patient's skin. Specifically, skin-attachment apparatus 32 includes flexible skin-attachment flap 34, secondary flap 66, and securing mechanisms 52, which serve to tighten the flaps against elongated member 26 when the mechanisms are engaged. Securing mechanisms may take the form of clips (such as small alligator clips), clamps, flaps that snap together, string, or any other suitable means of temporarily securing flaps 34 and 66 around elongated member 26 in a way that prevents elongated member 26 from moving relative to the flaps until securing mechanisms 52 are disengaged. Padding material, such as a sponge, gelatin-like material, or trapped air may be placed in spaces 68 defined by flaps 66, 34, and elongated member 26, in order to make attachment of skin-attachment apparatus 32 more comfortable to patients placed in supine positions.

Figure 6:
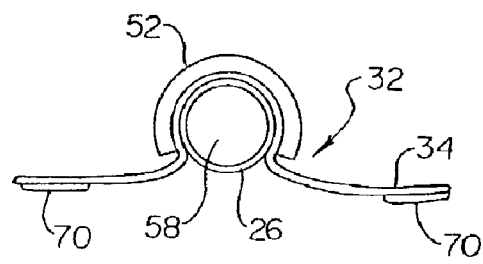
Figure 7:
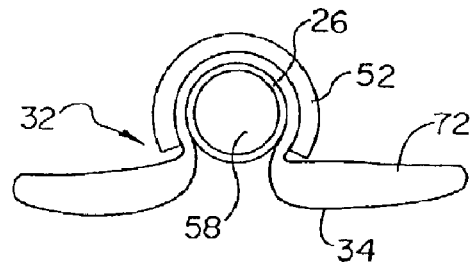
Figure 8:
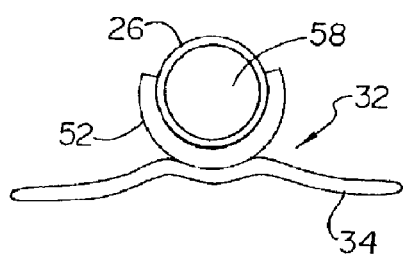

FIGS. 6-8 show skin-attachment apparatuses 32 coupled to elongated member 26 using only one securing mechanism 52. In addition, skin-attachment apparatus 32 in FIG. 6 includes adhesive 70, instead of openings 56 shown in other figures, that is useful in attaching flexible skin-attachment flap 34 to a patient's skin. In FIG. 7, flexible skin-attachment flap 34 contains padding material 72 (as may any of the present flexible skin-attachment flaps), which is useful as described above. In both FIGS. 6 and 7, flexible skin-attachment flaps 34 are positioned between elongated member 26 and securing mechanisms 52. In contrast, FIG. 8 shows that securing mechanism 52 may be in direct contact with elongated member 26. In the embodiment shown in FIG. 8, flexible skin-attachment flap 34 may be secured to securing mechanism 52 using any suitable means, including glue, integral formation, and the like.

Although not shown in FIGS. 4-9, it should be understood that a flexible skin-attachment flap 34 may be configured in the form of a flap that is folded over elongated member 26 and snapped together, the mating snaps serving as securing mechanism 52.

Figure 9:
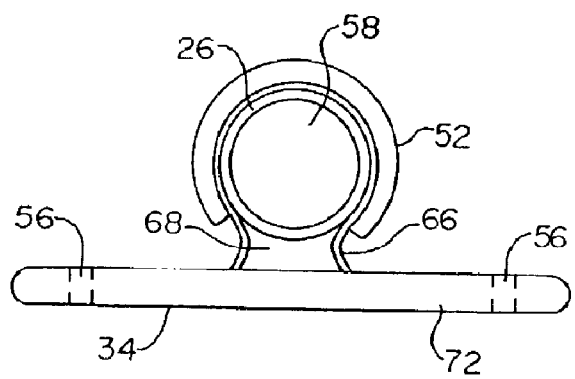

Turning to FIG. 9, the embodiment of skin-attachment apparatus 32 shown includes padding material 72 within flexible skin-attachment flap 34, and may include the same in space 68. Flaps 66 and 34 shown in both FIG. 5 and FIG. 9 may be attached to each other using any suitable means described in this document.

Figure 10:
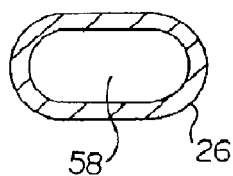
FIG. 10 is a cross-sectional view of an embodiment of an elongated member of one of the present medical devices suited for attachment to the skin, illustrating a non-circular shape.
Figure 11:
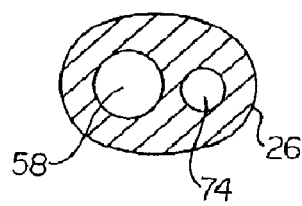
FIG. 11 is a cross-sectional view of an embodiment of an elongated member of one of the present medical devices suited for attachment to the skin, illustrating two passageways sized to slidably receive, and work with, at least a guidewire.
Figure 12:
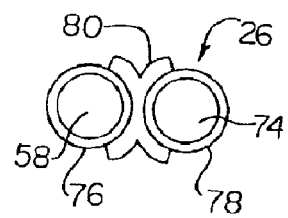
FIG. 12 is an end view showing two sub-elongated members coupled together.

FIGS. 10, 11 and 12 illustrate different embodiments of elongated member 26 of sheath 24. While these figures are described in terms of elongated member 26 and, hence, sheath 24, the embodiments discussed are equally applicable to devices such as catheter 42 depicted in FIG. 1, which may be introduced through the passageways discussed in FIGS. 10-12.

FIG. 10 illustrates a cross section of elongated member 26, revealing that it can have a shape at a given cross section that is non-circular. Advantageously, an elongated member 26 having such a shape along any portion of its length may be well-suited to navigating certain regions within the subarachnoid space that are wider in one dimension than in another. Suitable shapes of cross sections taken at a particular location along an elongated member include oval, and figure-eight shapes. Furthermore, the present elongated members, and the present sub-elongated members discussed below, may have cross-sectional shapes that vary along the length of the member.

FIG. 11 illustrates another cross section of elongated member 26, revealing that it can have both first passageway 58 and second passageway 74. Like first passageway 58, second passageway 74 can be sized to slidably receive, and work with, at least a guidewire. Moreover, elongated member 26 can have additional such passageways consistent with the present methods and apparatuses. Additionally, while the passageways described in this document (including the claims) may extend through openings that coincide with the ends of the particular devices in question (such as sheath 24 and catheter 42 shown in FIG. 1), the openings within the present medical devices that serve to define the present passageways may be located in positions other than the ends of the present medical devices. Thus, a sheath or a catheter that has one or both ends closed may nevertheless have a passageway as that term is used in this document (including the claims) so long as two openings to the outside of the device exist that serve to define the passageway. For example, one of the present devices could have a passageway defined by openings positioned within the wall of the device. In addition, two passageways could share a common opening, regardless of the location of the common opening. However, if the passageway in question is restricted to being sized to slidably receive, and work with, at least a guidewire, the positioning of the openings in question must satisfy this condition as well.

Turning next to FIG. 12, there is shown elongated member 26 having two sub-elongated members 76 and 78 that are coupled together using coupling device 80, which allows the operator to snap the pieces of tubing together. Other means for coupling sub-elongated members 76 and 78 may also be used, such as interlocking parts that are integrally formed with the sub-elongated, interlocking parts that are attached to the sub-elongated members, adhesives that serve to secure the sub-elongated members together but that allow them to be repositioned and re-secured, melting of the sub-elongated members together, glue, and the like. Alternatively, sub-elongated members 76 and 78 may be joined, as by bonding during manufacture, such that a cross-sectional configuration of them resembles that shown in FIG. 12, only without a coupling device 80 interposed between sub-elongated members 76 and 78. Sub-elongated member 76 has first passageway 58, and sub-elongated member 78 has second passageway 74. In this document (including the claims), "a sub-elongated member" can, but need not, have a perfectly round cross section. Thus, both sub-elongated members 76 and 78 could have cross sections at any location along their length with shapes like the ones depicted in FIG. 10.

Furthermore, as shown in FIG. 13A, sheath 24 can include elongated member 26, which can have sub-elongated members 76 and 78 that possess different lengths. As shown, sub-elongated member 76 has first end 28 and second end 30, and sub-elongated member 78 has first end 82 and second end 84. FIG. 13A also shows that valve apparatus 36 may be coupled to both sub-elongated members, as may be skin-attachment apparatus 32. Furthermore, end 84 is closed, and sub-elongated member 78 has an opening 86 located within the wall of sub-elongated member 78 that together with the opening at first end 82 of sub-elongated member 78 serves to define second passageway 74.

Figure 13H:
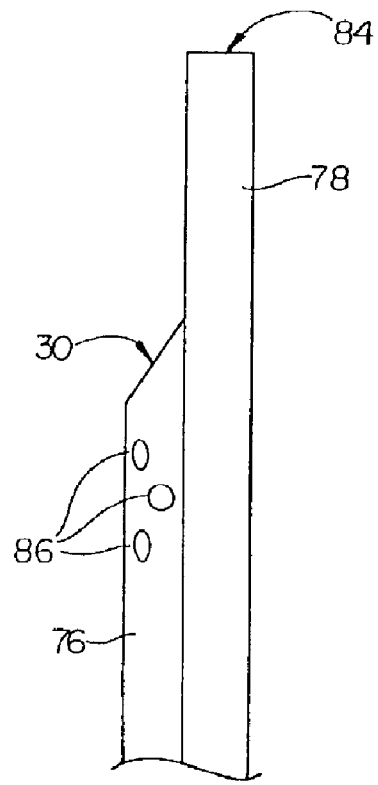

Moving ahead to FIG. 13H, the same shows that the sub-elongated members of sheath 24 depicted in FIG. 13A may alternatively be arranged such that one of the sub-elongated members has multiple openings 86, as shown in sub-elongated member 76. Sub-elongated member 76 has a closed second end 30 in FIG. 13H. As explained below, fluid may be introduced through one passageway to a desired location, and withdrawn through another passageway. The configuration of sheath 24 illustrated in FIG. 13H may be used during such a procedure.

FIGS. 13B-G illustrate different embodiments of the shapes of second ends 30 and 84 of sub-elongated members 76 and 78, respectively. FIG. 13B shows that second end 30 of sub-elongated member 76 may be offset from second end 84 of sub-elongated member 84. FIG. 13B also shows that second end 30 of sub-elongated member 76 may be beveled, or tapered, into sub-elongated member 80, thereby reducing the chance that sheath 24 will "hang up" on other structures prior to reaching its intended destination. This same benefit may be realized using the configuration of sheath 24 (via sub-elongated members 76 and 78) shown in FIGS. 13C, 13D, and 13G. The configurations illustrated in FIGS. 13E and 13F may be used as the application warrants.

Currently, catheters are available that have compound wall constructions that impart a variable stiffness along the length of the catheter. Catheters are also available with reinforcing material braided into the wall of the catheter to give the catheter greater strength and resistance to kinking. The present devices such as catheter 42 and sheath 24 may have lengths and stiffnesses that vary along those lengths, and they may have walls that include braided materials therein. Also, the present devices such as catheter 42 and sheath 24 may be bendable, and may retain a shape after being bent.

As those of skill in the art will understand, the size of a given passageway of one of the present devices (such as sheath 24 or catheter 42) may be sized appropriately for a given application. Diameters for a passageway within a given device (such as sheath 24, and specifically elongated member 26, and catheter 42) may, for example, be chosen from sizes that include 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, and 0.10 inches. These same dimensions may, for example, serve as the size of either the widest or most narrow dimension of a passageway of one of the present devices (such as sheath 24, and specifically elongated member 26, and catheter 42) that has a non-circular shape. The outer diameter of the present devices (such as sheath 24, and specifically elongated member 26, and catheter 42) may, for example, be chosen from sizes that include 1, 2, 3, or 4 millimeters. These same dimensions may, for example, serve as the size of either the widest or most narrow dimension of the outer surface of one of the present devices (such as sheath 24, and specifically elongated member 26, and catheter 42) that has a non-circular shape.

As explained with reference to FIG. 1, for example, the present devices (such as sheath 24 and catheter 42) enter the spinal subarachnoid space after passing through dural membrane 10. In order to close dural membrane 10 after a procedure is complete, the present devices (such as sheath 24, and specifically elongated member 26, and catheter 42) may have a dural closure apparatus coupled to it. The dural closure apparatus may be configured to be coupled to the device in question, and, in fact, may be coupled to it. The dural closure apparatus may be configured to close the dural membrane as the device is withdrawn from the spinal subarachnoid space. In one embodiment, the dural closure apparatus may be configured to effect closure through movement of a needle, or other suture-delivering apparatus, that is actuated by the operator to cause a suture to be placed through the dura. In another embodiment, the dural closure apparatus may be configured to effect closure through injection of a chemical compound that seals the hole in the dura after the device is withdrawn. One example of a dural closure apparatus that may be modified and coupled to one of the present devices is THE CLOSER (commercially-available from Perclose, Inc., an Abbot Laboratories Company, 400 Saginaw Drive, Redwood City, Calif. 94063).

Figure 19:
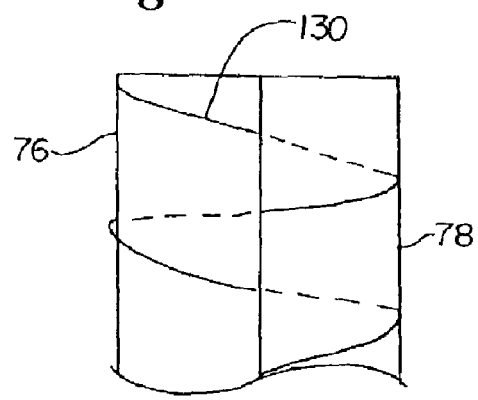
FIG. 19 is a partial side view depicting one embodiment of two sub-elongated members coupled together with a braiding material.
Figure 20:
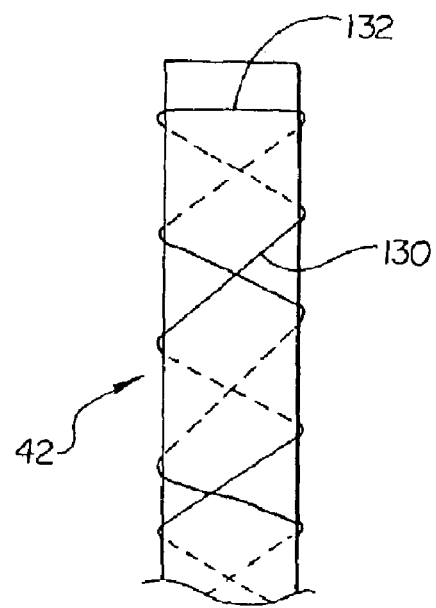
FIG. 20 is a partial side view depicting one embodiment of a catheter wrapped in braiding material.

FIG. 19 illustrates an embodiment of sheath 24 (which, of course, is equally applicable to catheter 42) in which sub-elongated elements 76 and 78 exist, wherein braiding material 130 (which can be a wire) is wrapped around both sub-elongated elements along the length of the sub-elongated elements (the total length not being shown). Such wrapping appears as a figure eight when viewed from the top. The braiding material may be wrapped as tightly or as loosely as the application warrants, and the tightness of the wrapping may vary along the length of sheath 24, thereby imparting the sheath with a variable stiffness and, therefore, flexibility. The same type of wrapping may be applied to a catheter having only one passageway, as illustrated in FIG. 20. There, the wrapping may be achieved using a single wire that is placed in contact with the wall of catheter 42 at roughly the midpoint 132. Then, the two halves of braiding material 130 may be crisscrossed to achieve the desired braiding, varying the tightness of the wrapping as desired to affect the stiffness of catheter 42. Alternatively, one end of braiding material may be placed in contact with catheter 42 near the end shown in FIG. 20, and the braiding may be achieved by winding the free end of the braiding material once around the catheter, then back up so as to cross the already-formed loop, then back down slightly further, and back up in the same fashion, repeating the process to achieve the desired braiding. Again, the tightness of the wrapping (which may be thought of as the closeness of the braiding material segments to each other) may be varied to vary the stiffness of the catheter.

The braiding pattern used may affect the MR-visibility of the resulting catheter or sheath. The subarachnoid space is filled with CSF that is relatively static and is of very high signal intensity on T2-weighted images. While a material that presents a signal void on MR could not be seen on either T1- or T2-weighted fluoroscopy in the vascular space (flowing blood has a signal void in either of these settings), a material that has a signal void is very conspicuous on T2-weighted imaging in the subarachnoid space. Platinum is a metal that is appropriate for enhancing the MR-visibility of the present devices. Additionally, other metals having low signal intensity may be appropriate. For example, there is a non-ferromagnetic form of stainless steel that is used in some needles for biopsy under MR guidance (Cook, Inc.). Also, there is an alloy of nickel and titanium (nitinol) that is used for guidewires and has been used in catheter braiding in the past (Target Therapeutics) that may have desirable signal characteristics. These materials may be used as markers on the present devices, and for braiding material 130. In addition, stainless steel, which is currently used in some catheter braiding by Cordis, may be used as braiding material 130. Kevlar may also be used for braiding material 130.

Medical devices such as sheaths and catheters that have the configurations discussed in FIGS. 11 and 12 (i.e., that have two or more passageways) may enable the use of an endoscope in one passageway to observe, for example, a manipulation conducted using a device introduced through the other passageway, or even the position of the other sub-elongated member that has the other passageway. Medical devices such as sheaths and catheters that have the configurations discussed in FIGS. 11 and 12 (i.e., that have two or more passageways) may also permit a fluid to be introduced in one passageway and withdrawn via the other passageway. Medical devices such as sheaths and catheters that have the configurations discussed in FIGS. 11 and 12 (i.e., that have two or more passageways) may allow the introduction of a guidewire in one passageway and another, therapeutic device in the other passageway. Interaction between functions conducted via each passageway may be achieved such that the functions work together, or compliment each other, to achieve a therapeutic goal.

Furthermore, medical devices such as sheaths and catheters that have the configurations discussed in FIGS. 11 and 12 (i.e., that have two or more passageways) have vascular applications, too. For example, there are currently instances in aneurysm treatment in which one catheter is introduced via one femoral artery for placement within an aneurysm and another catheter is introduced via the other femoral artery for introduction of a balloon across an aneurysm neck. Using a device other than a balloon to assist the aneurysm coiling, an apparatus may be introduced via one passageway of a medical device such as a sheath or catheter that has one of the configurations discussed in FIGS. 11 and 12 (i.e., that has two or more passageways) to improve an aneurysm neck while a coil is introduced via the other passageway, thus achieving via a single femoral artery access that currently requires bilateral access. Furthermore, this aneurysm embolization may be achieved using a sheath or catheter that includes 2 sub-elongated members whose distal portions are spaced apart from each other, as in a "Y" shape.

Figure 18:
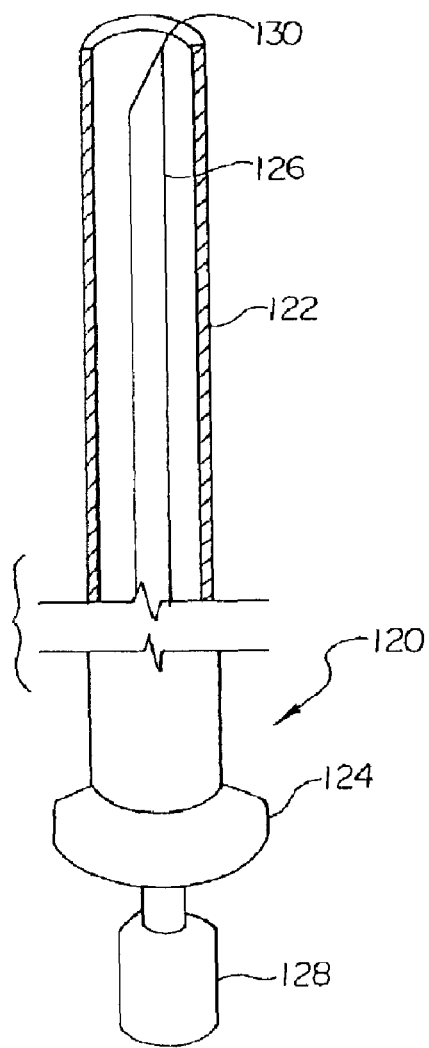
FIG. 18 depicts one embodiment of a penetration apparatus.

FIG. 18 illustrates a penetration apparatus 120 that is useful in penetrating various membranes that may be encountered using the present methods. Penetration apparatus 120 includes outer sleeve element 122, outer sleeve element hub 124 coupled to outer sleeve element 122, inner puncture element 126, and inner puncture element hub 128 coupled to inner puncture element 126. Outer sleeve element hub 124 may be configured to be slidably coupled to inner puncture element 126 (such that outer sleeve element 122 may slide along, and then be locked against, inner puncture element 126), and inner puncture element hub 128 may be configured to be slidably coupled to another device introduced through the passageway (not shown) of inner puncture element 126. Inner puncture element may be provided with a passageway sized to slidably receive, and operate with, at least a guidewire.

One membrane that may be punctured by operating penetration apparatus 120 is the pia mater—a membrane surrounding the brain that is fragile in some locations and tough in others. Distal tip 130 of inner puncture element may be configured to be sharp enough to penetrate the pia mater at any location therealong without exerting a degree of force or manipulation that results in either tearing of brain tissue or distortion of brain tissue prior to penetration. In operation, a device (such as sheath 24 or catheter 42) may be percutaneously introduced into the spinal subarachnoid space at an entry location, the device having a first passageway sized to slidably receive, and operate with, at least a guidewire; the device may be advanced within the subarachnoid space at least more than 10 centimeters from the entry location, or to facilitate intracranial access with a second device introduced through the first passageway; penetration apparatus 120 may be advanced through the first passageway of the device, and a membrane, such as the pia mater, may be punctured using penetration apparatus 120. More specifically, penetration apparatus 120 may be advanced along a guidewire, or it may simply be advanced through the first passageway, to the edge of the membrane; inner puncture element 126 may be further advanced until it punctures the membrane; inner puncture element may then be retracted into outer sleeve element 122 and penetration apparatus 120 advanced through the plane of the punctured membrane, or outer sleeve element 122 may be advanced over inner puncture element 126 through the plane of the punctured membrane. Outer sleeve element 122 may then act as a guidewire for a device such as catheter 42 as the same advances into the brain substance.

The material that may be used for the inner and outer elements of penetration apparatus 120 may, for example, be metallic or polymeric, such as plastic. Suitable materials for both outer sleeve element 122 and inner puncture element 126 include a nickel-titanium alloy, such as nitinol, that is treated to enhance its radiopacity. Alternatively, stainless steel may be used for either element, which can be plated with gold or platinum to enhance radiographic visibility. If an imaging modality such as MRI or radiographic visualization (e.g., fluoroscopy), that imaging modality used may impact the materials used in the construction of the elements of penetration apparatus 120.

Another embodiment of penetration apparatus 120 that is not shown in FIG. 18 differs from the embodiment shown in FIG. 18 in the manner in which the inner and outer elements 126 and 122 are interrelated. In this additional embodiment, inner puncture element 126 is coupled to outer sleeve element 122 with a mechanism that allows inner puncture element to be "fired," or advanced rapidly, a few millimeters to achieve rapid penetration. In yet another embodiment of penetration apparatus 120 not shown in FIG. 18, inner puncture element 126 is coupled to outer sleeve element 122 using threads to allow for finely-controlled advancement of inner puncture element 126.

The present methods will offer many advantages over conventional methods of surgically accessing the intracranial and spinal subarachnoid space, which have historically consisted of the skin incision, dissection to either the cranium or spinal bony covering, removal of some bone, and dissection through the meninges to gain access to the neurological structures. For example, the present methods will avoid a craniotomy and a brain retraction, which are typical for conventional approaches to brain surgery; the present methods will enable operators to surgically approach the brain from a remote location (such as from a lumbar puncture, for instance); they will make it possible to perform such surgery in an MR scanner without interference from magnets in the surgical field; they will allow access to areas of the brain that are difficult to reach from a craniotomy approach; and the present methods it may enable some types of procedures (subarachnoid space lavage, etc.) not easily performed via craniotomy.

Representative Applications of the Present Methods

The following representative applications may be performed using devices such as catheter 42 and sheath 24, and further using any embodiment of those devices depicted in FIGS. 1 and 10-13H. Thus, anytime that a device such as catheter 42 or sheath 24 is referenced below in relation to the representative applications, it will be understood that versions of that device depicted in FIGS. 10-13H may be used for the given application. Depending on the application, the devices used may be treated so as to maximize their visibility via a given imaging modality, such as MRI or radiography (e.g., fluoroscopy).

Furthermore, it will be understood that for a given application, it may be feasible to introduce one device into the subarachnoid space at one entry location, and later, or simultaneously, introduce another device into the subarachnoid space at a different entry location, thereafter using the devices together to achieve a therapeutic result. For example, in altering the temperature of at least some brain tissue, discussed below in greater detail, it may be possible to introduce a fluid through the passageway of one device introduced into the subarachnoid space (such as the spinal subarachnoid space) at one entry location, and withdrawing fluid through the passageway of another device introduced into the subarachnoid space (such as the spinal subarachnoid space) at another entry location. As another example, in flushing CSF as described below, it may be beneficial to use two passageways of a sheath or catheter having multiple passageways to deliver fluid to a target area. Further, this may be achieved using a sheath or catheter that includes 2 sub-elongated members whose distal portions are spaced apart from each other, as in a "Y" shape. Fluid may be withdrawn through the passageway of a device introduced at a different entry location, or fluid may be withdrawn through a third passageway within the sole sheath or catheter.

Flushing of Cerebrospinal Fluid to Help Alleviate Vasospasm

The present methods can be used in the treatment of subarachnoid hemorrhage. A major complication of subarachnoid hemorrhage is vasospasm, which is related to the presence of blood in the subarachnoid space surrounding cerebral blood vessels. One treatment that is used neurosurgically to help alleviate vasospasm entails the lavage of the cerebrospinal fluid within the subarachnoid space with both saline and with hemolytic agents to remove the blood. Using the present methods, it may be feasible from a percutaneous spinal approach to catheterize the subarachnoid space in the region of a hemorrhage or clot and perform lavage from that approach without craniotomy. For example, after introducing a device (such as sheath 24 or catheter 42 discussed in relation to FIG. 1) into the spinal subarachnoid space at an entry location, the device having a passageway sized to slidably receive, and work with, at least a guidewire, and after advancing that device within the spinal subarachnoid space a distance from the entry location, saline and/or material having hemolytic agents may be transferred through the passageway of the device toward the region of the hemorrhage or clot in order to flush the relevant cerebrospinal fluid. This flushing may also be achieved with a second device introduced through the passageway of the first device.

Modifying the Temperature of at Least Some Brain Tissue

The present methods can be used to modify the temperature of at least some brain tissue. Such a modification may be achieved by flushing selected brain tissue with a fluid that may be temperature-controlled, such as saline, which fluid is introduced through a device introduced into the spinal subarachnoid space. For example, after introducing a device (such as sheath 24 or catheter 42 discussed in relation to FIG. 1) into the spinal subarachnoid space at an entry location, the device having a passageway sized to slidably receive, and work with, at least a guidewire, and after advancing that device within the spinal subarachnoid space a distance from the entry location, the temperature of at least some brain tissue may be modified by introducing a temperature-controlled fluid, such as saline, through the passageway of the device to the selected brain tissue. This may be particularly effective using a device that has at least two passageways. The introduction of fluid in this manner may also be achieved with a second device introduced through the passageway of the first device.

One example of modifying the temperate of at least some brain tissue is inducing hypothermia in at least some brain tissue. The potential beneficial effects of hypothermia in protection against injury are well known, both in the public domain and in the medical literature. The most commonly encountered instance in the uncontrolled environment is probably in near drowning. In these situations, survival is enhanced in cold water because the metabolism is slowed and hypoxia is better tolerated.

In neurosurgical practice, hypothermia is used therapeutically to prolong cerebral vascular occlusion times that can be tolerated during aneurysm surgery. However, most traditional neurosurgical techniques are unable to create isolated cerebral hypothermia. Thus, whole-body hypothermia is used, often in association with circulatory arrest, with all the attendant risks.

A pumping apparatus may be utilized in the process of modifying the temperature of at least some brain tissue to assist in maintaining pressures and temperatures within the subarachnoid space. This pumping apparatus may be coupled to the device through which the fluid is introduced. This pumping apparatus may include 2 independently-controlled, calibrated pumps that may be coupled to a hub adapter coupled to, for example, the device through which the fluid is introduced. To control the intracranial fluid volume, the volume of fluid pumped into the subarachnoid space may be matched by an equal volume that is withdrawn from the subarachnoid space. This pumping apparatus may be configured to achieve this balance with flow monitors and flow controls, even in circumstances in which the outflow may be achieved without introducing negative pressure at the outflow site. Further, in this regard, this pumping apparatus may be configured to operate with pressure monitors and pressure controls that enable both the measurement of intracranial pressures and the manipulation of the same. In addition, this pumping apparatus may be configured to operate with temperature monitors and temperature controls that enable both the measurement of intracranial temperatures and the manipulation of the same. In this regard, the pumping apparatus may be configured to operate with temperature monitors and temperature controls that enable both the measurement of infused fluid temperatures and the manipulation of the same.

Flow rates as low as a fraction of a cubic centimeter per second or as high as multiple cubic centimeters per second may be achieved with this pumping apparatus, though pressures exceeding 200 millimeters mercury are considered unlikely since this would exceed intracranial pressures likely to be compatible with life. Infusate (i.e., infused liquid) temperatures varying between 32 and 110 degrees Fahrenheit may be achieved using this pumping apparatus.

Monitoring Physiologic and Biochemical Properties

Figure 14:
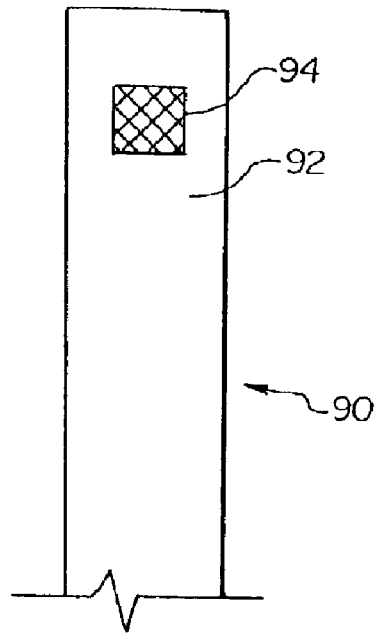
FIG. 14 is a partial side view illustrating a detector attached to the outside surface of one of the present medical devices.

The present devices that have passageways sized to slidably receive, and work with, at least a guidewire (including those illustrated as sheath 24 and catheter 42 in FIG. 1) may also have walls that have monitors therein. In this regard, FIG. 14 illustrates a portion of device 90 having wall 92 and detector 94 attached to wall 92. Detector 94, although shown as attached to the exterior of wall 92, may be embedded within wall 92 beneath the outer surface of wall 92 in certain embodiments, depending, for example, on the depth of detector 94 below the outer surface and the type of material from which wall 92 is made. In such an instance, device may be described as having wall 92 and a detector 94 "in" or "within" wall 92, or "therein." Further, wall 92 may have an opening, and detector 94 may be attached to the inside surface of wall 92 and extending across that opening, provided proper precautions are taken to avoid damaging detector 94 as device 90 is navigated. Additionally, the location of detector 94 may be varied, from being at an end of device 90, to being located at any position along wall 92.

Figure 15:
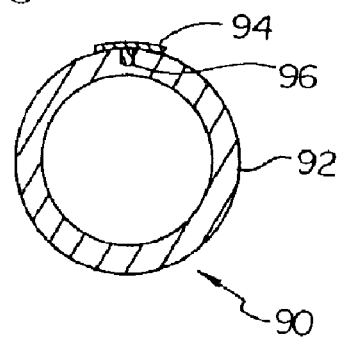
FIG. 15 is a cross-sectional view showing the detector depicted in FIG. 14 being coupled to a communication device illustrated as a wire positioned in the wall of the medical device.

Detector 94 may be an electroencephalography electrode useful for monitoring electrical activity (i.e., an attribute). Detector 94 may be a sensor useful for monitoring a biochemical property (i.e., an attribute) such as pH, glucose concentration, oxygen tension, carbon dioxide concentration, or sodium concentration. Thus, one of those biochemical properties may be monitored using the sensor. Detector 94 may be a thermal sensor useful for monitoring temperature (i.e., another attribute). Thus, temperature, such as of a fluid or a temperature, may be monitored using the thermal sensor. Detector 94 may also be useful for monitoring neurotransmitter concentration (i.e., an attribute). Thus, neurotransmitter concentration may be monitored using the detector. In this document (including the claims), an element such as a detector, which may take the form of a sensor, that is "useful for monitoring" something need only play a role in the monitoring, and need not completely perform all the steps necessary to achieve the monitoring. Also, in this document (including the claims), monitoring an attribute "using" a sensor or a detector means that the sensor or detectors is involved, or plays a role, in the monitoring, but need not be the only device used to achieve the monitoring FIG. 15 is a cross sectional view of device 90, showing that detector 94 may be coupled to a communication device that is illustrated as wire 96 embedded within wall 92. It will be understood to those of skill in the art having the benefit of this disclosure that the communication device (in this case, wire 96) may alternatively be secured to the outside surface of wall 92 as is detector 94, or to the inside of the wall. The communication device may travel along the length of device 90 any sufficient distance, and may exit, or extend away from, wall 94 at any suitable location, including prior to the end of device 90 that is not shown in FIG. 14, at a hub coupled (whether permanently or otherwise) to the end of device 90 that is not shown, at the end of device 90 that is not shown, and at a valve apparatus (such as valve apparatus 36 illustrated, for example, in FIG. 3) coupled to the end of device 90 that is not shown. The communication device can then be linked to a station that processes the signal from the detector that travels along the communication device and that is useful in monitoring and controlling the detected attribute. The pumping apparatus disclosed herein may include that station. The station may be configured to record data that it collects and/or generates in monitoring and/or controlling the detected attribute on any suitable media, including paper and electronic data. The communication device can also take the form of a wireless communication using, for example, radio waves or other electromagnetic means of transmission.

Figure 16:
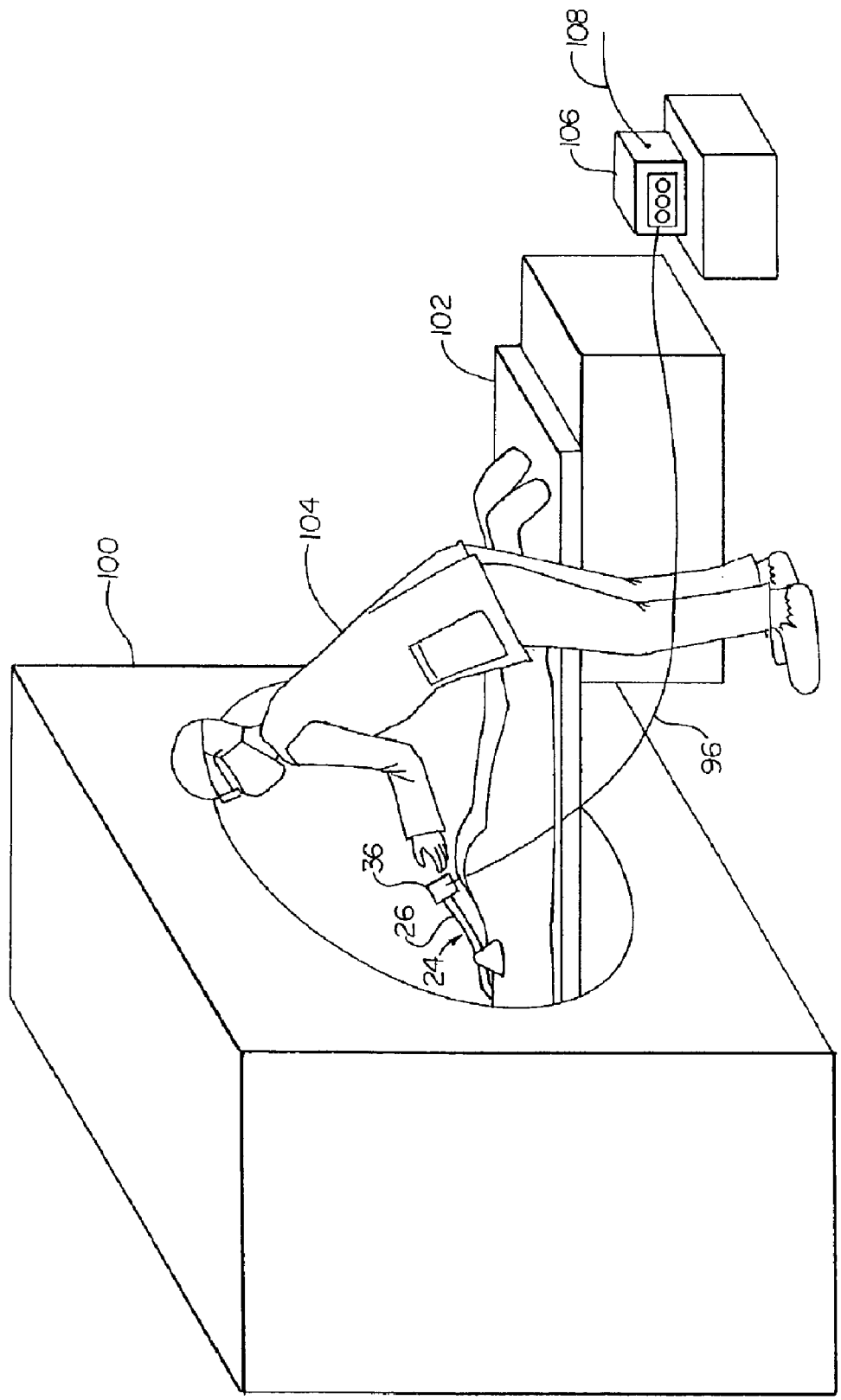
FIG. 16 illustrates an operator applying the present methods to a patient positioned within an MR scanner.

FIG. 16 illustrates some of the benefits of the present methods. FIG. 16 illustrates a patient positioned in MR scanner 100 and on top of sliding table 102. Operator 104 is positioned remotely from the target area being scanned such that the magnets within MR scanner 100 do not interfere with his or her manipulations. Sheath 24 is shown as being inserted into the patient, and a communication device illustrated as wire 96 is shown traveling from outside of valve apparatus 36 to station 106. Wire 96 is coupled to a detector (not shown) attached to the wall of the elongated member 24. The hidden detector may be an electroencephalography electrode useful for monitoring electrical activity. The hidden detector may be a sensor useful for monitoring a biochemical property such as pH, glucose concentration, oxygen tension, carbon dioxide concentration, or sodium concentration. The hidden detector may be a thermal sensor useful for monitoring temperature. The hidden detector may also be useful for monitoring neurotransmitter concentration. Station 106 may be configured to record data that it collects and/or generates in monitoring and/or controlling the detected attribute on any suitable media, including paper and electronic data. Also, a second communication device in the form of wire 108 is illustrated as exiting station 106 and traveling to an undisclosed area where another operator can view the data generated and collected by station 106.

Figure 17:
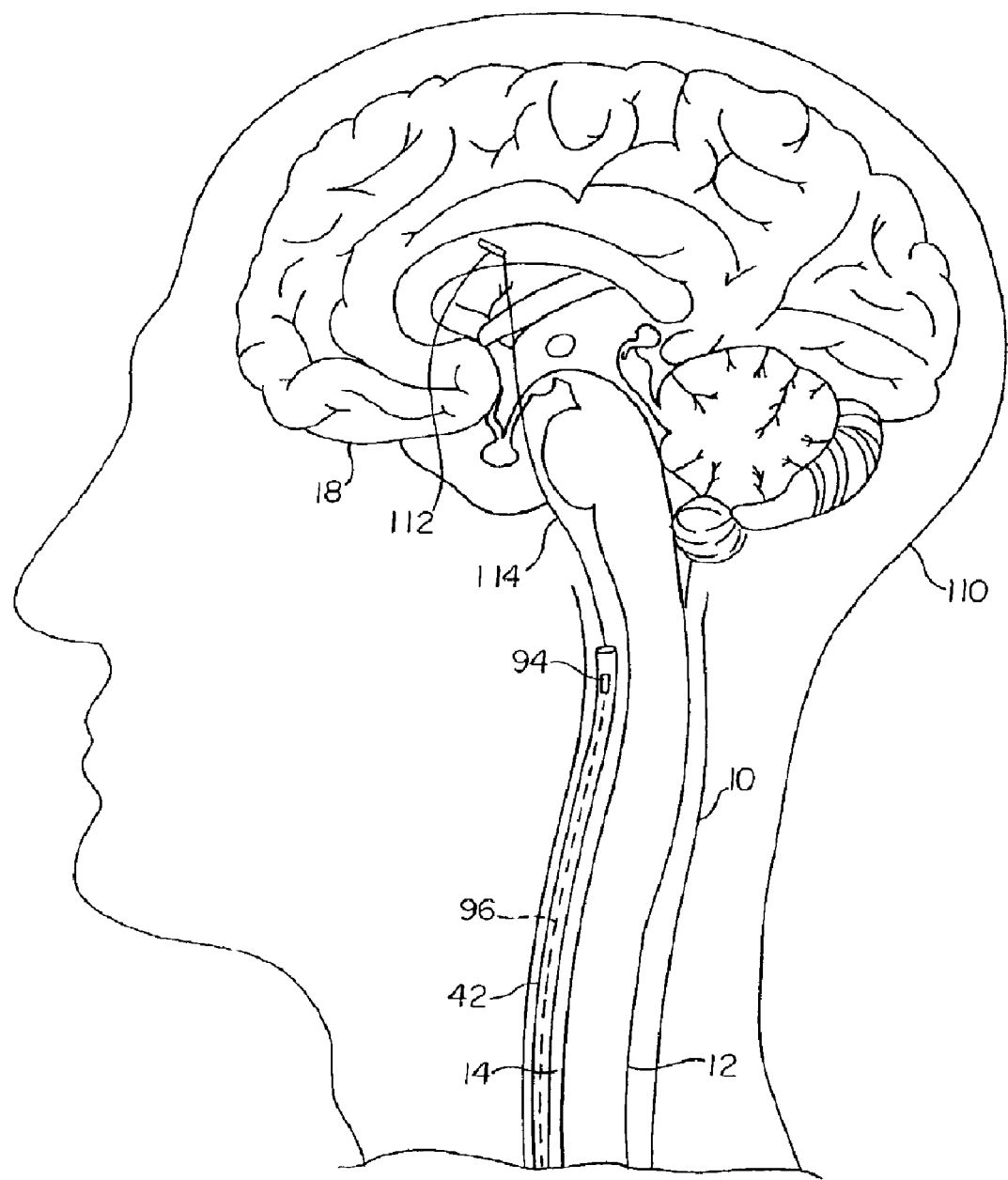
FIG. 17 illustrates a detector being placed in brain tissue using the present methods.

The same types of monitoring that may be achieved using a detector attached to a device such as sheath 24 or catheter 42 (which is illustrated in the form of device 90 in FIG. 14), may also be achieved using a detector or detectors implanted in brain tissue or in the subarachnoid space. FIG. 17 illustrates detector 112 that is positioned intracranially. FIG. 17 shows brain 18 inside of head 110, and further shows that catheter 42 may have a wall in which detector 94 is located. FIG. 17 also illustrates that a communication device in the form of wire 96 is coupled to detector 94 and embedded within the wall of catheter 42, as indicated by the dashed lines. A detector delivery mechanism illustrated as wire 114 is shown as being coupled to detector 112. This coupling may be achieved through any suitable means, including electromagnetic means, and mechanical means such as clips, and temperature- or pressure-sensitive adhesives, and the like. Detector 112 may be coupled to wire 114 in a way that will allow the detector to be detached from wire 114 once detector 112 has reached its intended destination. In such an embodiment, detector 112 may wirelessly communicate with a station like station 106 illustrated in FIG. 16. Alternatively, the detector delivery mechanism illustrated as wire 114 may remain coupled to detector 112 and serve as a communication device between detector 112 and a remote station. In any embodiment, detector 112 should be configured to slidably move within the passageway of catheter 42. Devices, such as catheter 42, may have passageways at least as large as 0.016" in the widest dimension and may be used to introduce detectors 112 to a desired location. Detector 112 may include an anchoring mechanism for retaining its position once delivered. This includes an anchoring mechanism that deploys once detector 112 exits catheter 42; such an anchoring mechanism may have a non-tubular configuration. For example, one suitable anchoring mechanism that is also used in vascular systems involves "hooks" or "barbs" located at the tips of wire members of devices, which hooks engage the walls of vessels to hold the device in place. Such hooks may also be used as an anchoring mechanism to engage the dura in instances in which detector 112 is implanted in the subarachnoid space. Another suitable anchoring mechanism would be a flared end on detector 112, resembling conventional flared configurations on the tips of conventional ventricular shunt catheters. Such an anchoring mechanism would be useful in instances in which a detector 112 is placed either in brain tissue or in a catheter destined for a ventricle. Like detector 94, detector 112 may be an electroencephalography electrode useful for monitoring electrical activity. Detector 112 may also be a sensor useful for monitoring a biochemical property such as pH, glucose concentration, oxygen tension, carbon dioxide concentration, or sodium concentration. Detector 112 may be a thermal sensor useful for monitoring temperature. Detector 112 may also be useful for monitoring neurotransmitter concentration.

In addition to the embodiments illustrated in FIGS. 14, 15, and 17, multiple detectors 94 may be attached to the inside or outside surfaces of the wall of one of the present devices (such as sheath 24 or catheter 42), or placed within the wall of one of the present devices, in order to better monitor the various attributes discussed above. Thus, 2, 3, 4, 5, 6, 7, 8, 9, 10, or more detectors may be placed on or in one of the present devices. Furthermore, a single communication device (such as wire 96) may be used to link multiple detectors to a station. Additionally, each of the sub-elongated members illustrated in FIG. 13 may be provided with the detectors discussed above, in the manners discussed above. Thus, and by way of example, both of the sub-elongated members shown in FIG. 13 may have walls that have detectors attached to them, and the lengths of those sub-elongated members may be such that the detector attached to one sub-elongated member may be placed in brain tissue and may be useful for monitoring oxygen tension, while the detector attached to the other sub-elongated member may be placed in cerebrospinal fluid and may be useful for monitoring sodium concentration.

Placement of Electroencephalography Electrodes

As discussed above, detectors that are electroencephalography (EEG) electrodes may be introduced into the subarachnoid space in both the spinal and intracranial regions, and in brain tissue using the present methods. By way of explanation, in epilepsy treatment, it is often difficult to localize the site of a seizure focus. One technique used in particularly difficult cases involves placement of EEG electrodes either directly on the surface of the brain (electrocorticography) or within the brain substance (depth electrode implantation). Since EEG monitoring involves detection of extremely weak electrical signals that are emitted from brain cells, elimination of interference from scalp muscles, elimination of signal resistance from the skull bone, and placement of electrodes closer to the brain tissue emitting those signals is one way to increase the sensitivity and specificity of localization and detection.

While increasing the sensitivity and specificity of epileptiform activity detection, such techniques as electrocorticography and depth electrode implantation have traditionally been invasive, requiring either burr holes in the skull for depth electrode placement or craniotomy for cortical array placement in electrocorticography. If bilateral monitoring is desired, bilateral burr holes or craniotomies have been necessary.

However, using the present methods, which involve percutaneous access to the subarachnoid space, usually in the lumbar region, followed by placement of devices such as sheath 24 and catheter 42, EEG electrode placement may be achieved, for example, in the cerebral subarachnoid space after entry via the foramen magnum. EEG electrodes may be placed on the surface of the brain or within brain tissue using the present methods.

In instances in which EEG electrodes take the form of detectors 112 discussed above with respect to FIG. 17, multiple detectors may be linked with a single communication device (also discussed above) that takes the form of a wire. Multiple wire and detector(s) combinations may be placed during a single procedure, and the different wires may have different diameters, different stiffnesses, or the like. Thus, arrays of EEG electrodes may be placed on or within brain tissue to map out the electroencephalogram from the deep brain structures. As an exemplary description of the manner of placing multiple EEG electrodes, a catheter having two passageways may be advanced to a desired location over a guidewire positioned in one of the two passageways. An EEG electrode may then be placed in a desired location through the open passageway. After placement, the catheter may be withdrawn over the guidewire, leaving the guidewire and the first EEG electrode in place. The catheter may then be reintroduced over the guidewire, and a second electrode placed in a desired location through the once-again open second passageway. This process may be repeated as many times as necessary.

In instances in which the EEG electrodes take the form of detectors 94 discussed above with respect to, for example, FIG. 14, multiple detectors may be linked with a single communication device (as discussed above) that takes the form of a wire, and multiple wire and detector(s) combinations may be attached to a device such as sheath 24 or catheter 42. Furthermore, one or more wire and detector(s) combinations can be attached to guidewires such as guidewire 44 shown in FIG. 1.

Spinal and Cerebral Stimulation

There are situations in medicine and in research where it is desirable to deliver an electrical impulse to the brain and spinal cord. Using the present methods, an electrode suited to such stimulation may be placed, thereby enabling the application of electric current, heat, or cryothermal stimulation of a patient's tissue. Such electrodes may be configured the same way as detectors 94 and 112 discussed above—that is, they may be attached to, or placed within, the wall of a device such as sheath 24 or catheter 42, or they may not be associated with a device, such as can be achieved using detector 112. Furthermore, a transmission device such as a wire may be coupled to the electrode (and either attached to a device like sheath 24 or catheter 42, or not attached in that fashion, depending on the application) to introduce the stimulating signal to the electrode. However, the stimulating signal may also be introduced to the electrode via a wireless transmission. Furthermore, in certain embodiments in which a transmission device such as a wire is used, the wire may be linked to a station useful in delivering the stimulating signal, and that is located outside of the patient's body or implanted within the patient, such as a station that is implanted in the subcutaneous space of the patient. Such stations currently exist in cardiac pacemakers and in transcutaneous neural stimulation devices used for pain control.

Implantation of Radioactive Pellets, or Beads, for Treatment of Tumors

The present methods can be used to implant radioactive pellets, or bead, into patients, in areas such as the brain, in order to irradiate a tumor. While the use of radioactive pellets for tumor irradiation is known, the placement of such pellets using the present methods is novel. As with all the other applications that may be achieved using the present methods, the placement of radioactive pellets may be monitored under direct MR visualization. Further, a series of pellets may be implanted into patients using a smaller introduction apparatus than is currently utilized for placing the pellets using conventional techniques.

Ablation of Brain Lesions

In functional neurosurgery, it is sometimes desirable to create lesions in the brain. This is seen in chronic pain syndromes, Parkinson's disease, and other settings. Current techniques for creation of these lesions involve CT- or MR-guided stereotaxis, in which a cryothermal or thermal ablation device is introduced to the desired location in the brain via a burr hole in the skull that the neurosurgeon drills in the operating room.

Using the present methods, a device (such as sheath 24 or catheter 42) or a guidewire (such as guidewire 44) may be introduced into the subarachnoid space (for example, the spinal subarachnoid space) and advanced as described above with respect to FIG. 1 to a desired location. Energy, such as thermal energy or cryothermal energy, may then be applied either to an ablation device imbedded in or attached to the catheter, sheath, or guidewire or to an ablation device introduced through the passageway of the catheter or sheath such that a lesion is created in the adjacent tissue, such as brain tissue. Other areas of application include tumors that may be in locations that are either inaccessible via conventional techniques, or that require unacceptable morbidity to approach them via conventional techniques. Such locations may include locations in the brain stem, the spinal cord, or in the subarachnoid space. In cases in which the ablation device is attached to or embedded within a device or a guidewire, the ablation device may be positioned at the end of the device or guidewire, or it may be positioned at any suitable location along the length of the device or guidewire.

By using one or more imaging modalities to monitor the therapy resulting from the ablation may make it feasible to create a lesion, observe partial success, and enlarge the lesion without repositioning the introducing device (such as catheter 42), or with minimal manipulation of the introducing device. Furthermore, tissue ablation achieved using the present methods may be performed in conjunction with conventional surgery such that lesions are created either before or after conventional resections, either to enhance the resection preoperatively or to improve margins of incompletely-resected lesions, or to provide an alternate approach to large-scale resections in diseases with multiple brain lesions such as metastatic disease from different forms of malignancy.

Accessing One or More Ventricles

In medicine, the ventricular system is frequently catheterized, both temporarily (ventriculostomy) and permanently (shunting). This occurs to combat hydrocephalus, to monitor pressure and, less often, for introduction of various medications or withdrawal of cerebrospinal fluid. However, the current neurosurgical approach requires placement of a burr hole in the skull bone and insertion of the catheter through the brain tissue—usually the frontal or parietal lobe—to access the ventricles.

Using the present methods of percutaneous subarachnoid navigation, the lateral ventricles, the $3^{rd}$ ventricle, and the $4^{th}$ ventricle may be accessed via medical devices such as catheter 42 or guidewire 44. Accordingly, using the present methods, at least one ventricle located within the head may be accessed. Imaging modalities may be used as described above (and with all the movements of medical devices described herein) to monitor the position of such devices as they approach and enter a ventricle.

Furthermore, using the present methods, at least one ventricle located within the head may be drained. For example, in applications involving shunting, there will be a need for placement of a shunt component in the peritoneal cavity or venous return to the heart. This may be accomplished using the present methods. Specifically, after percutaneously introducing a device (such as sheath 24 or catheter 42) into the spinal subarachnoid space at an entry location, the device having a first passageway sized to slidably receive, and operate with, at least a guidewire, and advancing the device within the subarachnoid space at least more than 10 centimeters from the entry location, or to facilitate intracranial access with a second device introduced through the first passageway, one or more ventricles located within the head may be accessed and/or drained. The draining may be achieved using a commercially available mechanism that spans a ventricle and a drainage location, and that acts as a one-way valve that allows that CSF and other fluid to flow in one direction—away from the ventricle or ventricles in question.

Brain Biopsies

The brain is a very soft and gelatinous tissue once the membrane surrounding it (pia) is penetrated. Neurosurgeons resecting brain often use a tubular apparatus attached to suction to aspirate brain tissue rather than cutting it with a scalpel or scissors. That quality of brain tissue should lend it to biopsy by way of aspiration.

Using the present methods, a device may be introduced through the passageway of a device such as catheter 42 or sheath 24 that may be used to remove a part of the brain. For example, the device that may be used to remove a part of the brain may be a traditional stereotactic device that is configured for introduction through the passageway of a device such as catheter 42 or sheath 24.

Alternatively, a device such as catheter 42 or sheath 24 may be coupled to suction by was of a syringe or other mechanism, and used to retrieve a sample of tissue located at the tip of the catheter or sheath. Another feature of biopsies is that often multiple samplings of tissue are required to retrieve diagnostic material. Hence, it may be necessary to reposition the catheter or sheath for more than one biopsy sample. Once the device has been positioned the first time, it is desirable to avoid having to repeat the navigation that was performed to achieve initial positioning. Thus, using an embodiment of the sheath or catheter that has two passageways, an operator may be able to use the sheath or catheter in the manner discussed above with respect to EEG electrode placement. That is, the sheath or catheter may be positioned proximate (i.e., near) a target area, suction may be applied to an open passageway to retrieve a portion of the brain. The sheath or catheter may then be removed along the guidewire used to initially facilitate placement (leaving the guidewire in position), and if the tissue sample is inadequate, the catheter or sheath can be repositioned over the guidewire and another biopsy sample can be obtained in a similar manner. Without the retention of the guidewire via the one of the two passageways, it would be necessary to reposition from scratch, repeating whatever risk or difficulties were encountered during the first catheter or sheath placement.

Treating Neurologic Conditions

Using the present methods, genetic material may be introduced through the passageway of a device such as catheter 42 or sheath 24 and placed within a patient suffering from a neurologic condition in order to assist in treating that neurologic condition. Such genetic material may include human stem cells.

Furthermore, neurologic conditions arising from pressure on cranial nerves may also be treated using the present methods. For example, the present methods may be used to perform microvascular decompressions. In such an application, a device (such as sheath 24 or catheter 42) may be percutaneously introduced into the spinal subarachnoid space at an entry location, the device having a first passageway sized to slidably receive, and operate with, at least a guidewire; the device may be advanced within the subarachnoid space at least more than 10 centimeters from the entry location, or to facilitate intracranial access with a second device introduced through the first passageway; and a second device (which may be described as "material") may be introduced through the first passageway and placed between a vascular loop and one or more cranial nerves (which may take the form of placing the device proximate a cranial nerve) in order to relieve compression of the cranial nerve by the vascular loop. Furthermore, a second device may be introduced through the first passageway and used to cut a nerve, such as a cranial nerve.

Vascular Coagulation or Cauterization

Using the present methods, vessels may be coagulated at the time of surgery, either because they are observed to bleed or in order to prevent bleeding. Specifically, a device (such as sheath 24 or catheter 42) may be percutaneously introduced into the spinal subarachnoid space at an entry location, the device having a first passageway sized to slidably receive, and operate with, at least a guidewire; the device may be advanced within the subarachnoid space at least more than 10 centimeters from the entry location, or to facilitate intracranial access with a second device introduced through the first passageway; and an apparatus that is or that is like a "two-point" or "Bovie" apparatus (which are used in conventional surgery or neurosurgery) configured for introduction through the first passageway may be introduced through the first passageway and used to coagulate a vessel.

In conventional surgery, a metallic electrode is applied to a bleeding vessel and a current is applied through the electrode that heats the tissue such that the vessel is cauterized. That cauterization is achieved with the "two-point" apparatus via approximation of the points of a forceps, thus completing the current loop. However, monopolar cautery apparatuses also exist, and may be configured for introduction through the first passageway of a device introduced as described above.

Thus an apparatus having a cauterization element and a transmission device (such as a wire, an insulated wire, a wire loop, or an insulated wire loop) connected to the cauterization element that is configured for attachment to a current-inducing apparatus may be used with the present methods to apply heat to a vessel, thereby cauterizing or coagulating it. Alternatively, the apparatus may include a set of forceps positioned at the end of a guidewire as the cauterization element, which forceps would function to open and close and act similarly to the forceps on conventional "two-point" devices. The apparatus should be configured for introduction through the first passageway (as discussed above), or it should be combined with one of the present devices, such as catheter 42 or sheath 24, in the manner that detector 94 discussed above may be attached to device 90. The transmission device may be attached to one of the present devices (including a guidewire) in the same manner discussed above with respect to wire 96. The transmission device that is part of this apparatus may be a wire loop that flares slightly after it exits the passageway through which it is introduced.

Hence, using the present methods, a device (such as sheath 24 or catheter 42) may be percutaneously introduced into the spinal subarachnoid space at an entry location, the device having a first passageway sized to slidably receive, and operate with, at least a guidewire; the device may be advanced within the subarachnoid space at least more than 10 centimeters from the entry location, or to facilitate intracranial access with a second device introduced through the first passageway; and an the aforementioned apparatus configured for introduction through the first passageway may be introduced through the first passageway, current may be introduced to the cauterization element, the cauterization element applied to a selected vessel tissue, and coagulation achieved.

Cadaver Studies

Materials and Methods

Two recently deceased, unembalmed male human cadavers were placed in prone positions. Using fluoroscopic guidance, lumbar punctures were performed in each subject at both the L3-4 and L4-5 interspaces using a standard, single-wall puncture angiography needle. A 0.038 inch guidewire was then introduced and directed superiorly. Subsequently, a 5 French (F) angiographic dilator was advanced into the subarachnoid space over the guidewire to dilate the tract, and a 5 F arterial sheath was placed with its tip directed superiorly. In each cadaver, one sheath was subsequently used for catheterization posterior to the spinal cord and the other was used for catheterization anterior to the spinal cord.

Following sheath placement, angiographic techniques were applied to the subarachnoid space. Specifically, under fluoroscopic guidance a hydrophilic-coated angle-tipped guidewire (Radifocus→Glidewire, Terumo, Inc., Tokyo, Japan, distributed by Meditech→Boston Scientific Corp., Watertown, Mass.) was advanced with its tip directed either anteriorly or posteriorly under operator control. Care was taken to maintain a midline position whenever possible, but it could not always be maintained. The advancement was performed with inflation of the subarachnoid space via saline infusion. The pressure of the infusion was easily controlled via management of the height of the flush bag above the patient's spine, though the pressures of the infusion and of the subarachnoid space were not specifically monitored.

After entering the cranial space, manipulations with the catheters were undertaken to explore areas for catheterization. Following catheterization manipulations, the catheters were left in place for subsequent dissection. The sheaths were cut at the skin with the introducers and microcatheters in place using standard wire cutters. The stumps of the systems were then oversewn and the cadavers were embalmed.

Following embalming, one cadaver was examined for evidence of spinal cord injury from the catheterization process. Laminectomy was performed throughout the cervical and thoracic spine and extended inferiorly to the point of catheter entry. The opened dura was photographed with the catheters in place. The spinal cord was removed and photographed with the ventral catheter in place. Brain dissections were performed to confirm catheter locations and to examine for unanticipated injury to brain tissue, with specific attention to the optic chiasm region in the case of catheters which passed through that region.

Results

In each case, the guidewire advanced relatively easily through the thoracic and cervical spine. In some cases, the catheter was advanced readily without guidewire placement. Once at the foramen magnum, attempts were made with the posterior catheters to enter the $4^{th}$ ventricle. Observation was made during these attempts that navigation of the retrocerebellar space in the posterior fossa occurred relatively easily, on some occasions circum-navigating the posterior fossa to a position anterior to the pons. Also, advancement superiorly behind the cerebellum to the level of the tentorium occurred relatively easily. In each cadaver, a tough membrane was encountered at the base of the skull when midline catheterization was attempted. Whereas deflection of the guidewire for lateral or posterior catheterization occurred easily, the soft tip of the guidewire was inadequate for penetration of the membrane in the midline and the stiff end of the guidewire was used to penetrate the membrane. Subsequently, catheterization superiorly proceeded easily. In Cadaver 1, the posterior fossa catheter ultimately traversed the cerebellum during an attempt at fluoroscopically-directed $4^{th}$ ventricular catheterization. In Cadaver 2, the $4^{th}$ ventricle was successfully catheterized and injected with contrast, as described below.

Attempts were made without complete success to determine the location of the $4^{th}$ ventricle using only fluoroscopy. Contrast injections resulted in intracranial spilling of contrast without outline of cerebellar structures. Blind passes with the catheter to where the $4^{th}$ ventricle should be resulted in successful catheterization of the $4^{th}$ ventricle in one of the two subjects. This was confirmed with contrast injection showing filling of the $4^{th}$ ventricle, retrograde flow into the aqueduct of Sylvius, flow into the $3^{rd}$ ventricle, and subsequent flow into the frontal horns of the lateral ventricles bilaterally via the foramina of Munro.

In both subjects, catheterization of the subarachnoid space anterior to the pons occurred easily. Catheters as large as 5 F were successfully advanced to this position. At the upper pontine level, a tough membrane was encountered in both subjects that would not permit higher catheterization using standard techniques. In both cases, the guidewire was deflected repeatedly from that location, regardless of multiple catheter repositioning attempts. Therefore, the guidewire was reversed and the stiff end of the guidewire was used to "punch" through this membrane. The membrane was believed to be the membrane of Lilequist, though this could not be confirmed with certainty subsequent to the dissection. Once it was crossed, catheterization to the suprasellar cistern with the standard end of the microguidewire (Radifocus™ Guide Wire M, Terumo, Inc., Tokyo, Japan, Tapered Glidewire Gold™ 0.018-0.013 inches, distributed by Target Therapeutics→Boston Scientific Corp., Fremont, Calif.) proceeded smoothly. A Transit® 18 microcatheter (Cordis® Endovascular Systems, Johnson & Johnson, Miami Lakes, Fla.) was used in most cases, using in some cases a Tracker™ 38 catheter (Target Therapeutics® Boston Scientific Corp., Fremont, Calif.) as a guide catheter. In Cadaver 1, a single 4 F introducer catheter was used that came from a company bought by Medtronics (MIS, Inc., Sunnyvale, Calif.) that is now no longer commercially available. With that catheter, the introducer catheter was advanced to the suprasellar cistern.

Once in the suprasellar cistern in Cadaver 1, advancement of the catheter was relatively easy, and catheterization of the sylvian fissure was observed and confirmed when contrast was injected and seen to flow dependently within the fissure. The catheter was left in that position and the subject was embalmed.

In Cadaver 2, catheterization of the suprasellar cistern was followed by experimentation regarding the degree of control had over placement. First, the frontal fossa on the side opposite from the previously catheterized middle fossa was catheterized. The catheter was advanced along the orbital roof and observed to curve superiorly, with its tip ultimately anterior to the frontal lobe and deep to the frontal sinus. The catheter was then withdrawn to the location on the orbital roof and this was confirmed with contrast injection. Next, that catheter was repositioned and the contralateral floor of the middle cranial fossa was catheterized and confirmed with contrast injection.

The posterior fossa catheter was then advanced and seen to be in the $4^{th}$ ventricle, as described above. After contrast injection, some opacification of the $3^{rd}$ ventricle was seen. This opacification was used as a "road map" for the anteriorly placed catheter and attempts were made to catheterize the $3^{rd}$ ventricle directly through the region of the interpeduncular cistern (with fluoroscopy, the exact position was not identified). The pial lining of the undersurface of the brain resisted perforation with the soft end of the guidewire and the ventricle was elevated by the attempt but not punctured. Ultimately, however, the $3^{rd}$ ventricle was entered successfully, as evidenced by drainage of the retained contrast. This was subsequently confirmed directly by contrast injection through the $3^{rd}$ ventricular catheter. This subject was then embalmed.

Cadaver 1 was the only subject in which the spinal component of the catheterization was examined anatomically. Following full spinal laminectomy from the upper cervical area to the area of puncture in the lumbar spine, the posterior dura was incised and reflected. The dorsal introducer catheter was seen lying superficial to the spinal cord without apparent spinal cord violation or laceration. This was then removed and the spinal cord was resected by cutting the nerve roots bilaterally and lifting it out, retaining the ventral catheter with the spinal cord. It was observed to traverse anterolaterally, weaving anterior and posterior to different nerve roots. Again, there was no apparent spinal cord violation or laceration.

In Cadaver 1, anatomic exposure of the brain was preceded by latex impregnation of the vasculature following decapitation, with arteries impregnated with red latex and veins impregnated with blue latex. Dissection was performed via extensive bone drilling of the left frontotemporal area to reproduce an expanded surgical approach to the sylvian fissure and the region of the basilar apex. Exposure using an operating microscope revealed the microcather anterior to the midbrain, between the clivus and midbrain. It was followed inferiorly as it migrated to the right side of the basis pontis. There was no apparent violation of cerebral structures by the catheter during its passage anterior to the brain stem. The catheter traversed laterally in a sulcus in the left sylvian fissure. Removal of the temporal lobe revealed the catheter in the sylvian fissure, near branches of the middle cerebral artery. The posterior fossa catheter was observed to enter the cerebellum and was not pursued via further detailed dissection.

Dissection of Cadaver 2 revealed the 3$^{rd}$ ventricular catheter to be in place as suspected from the radiographs, located within the 3$^{rd}$ ventricle. The catheter was seen passing anterior to the brain stem along the clivus without brain stem penetration. Also, the basilar artery was seen separate from the catheter. The point of penetration of the 3$^{rd}$ ventricle was essentially vertical in the midline from the interpeduncular cistern. The 4$^{th}$ ventricular catheter was under some tension and sprang laterally as the cerebellum was split in the midline and its exact location could not be reconstructed. However, based on the images during contrast injection, it appeared to lie in the cerebellar tissue in the roof of the 4$^{th}$ ventricle.

All of the present methods and devices disclosed and claimed herein can be made and executed without undue experimentation in light of the present disclosure. While this invention has been described in terms of specific embodiments, the described embodiments are not exhaustive, and it will be apparent to those of skill in the art that other variations exist. For example, the flexible member portion that extends away from a skin-attachment apparatus (and thus away from a patient) should enhance robotic applications in angiography similarly to their enhancement of robotic access of the subarachnoid space. Also, the flexible member portion enables angiographic applications in which the sheath is placed in a femoral artery and the patient is rolled into a supine position for intraspinal or other surgical access posteriorly while retaining anterior arterial access for angiography via the flexible member portion, which can be placed out from under the patient.

REFERENCES

The following references, to the extent that they provide exemplary procedural or other details supplementary to those set forth herein, are specifically incorporated herein by reference.

Amar et. al., "Microcatheterization of the cervical epidural space via lumbar puncture: Technical note," *Neurosurgery*, 48(5):1183-1187, 2001.
Eguchi et. al., "Endoscopy of spinal cord and posterior fossa by a lumbar percutaneous approach: endoscopic anatomy in cadavers," *Minim. Invas. Neurosurg.*, 42(2):74-78, 1999.
Fries et. al., "Biportal neuroendoscopic microscurgical approaches to the study of subarachnoid cisterns. A cadaver study," *Minim. Invas. Neurosurg.*, 39(4):99-104, 1996.
Stefanov et. al., "A new method for transcutaneous coaxial neuroendoscopy," *Anat Embryol* (Berl), 194(4):319-26, 1996.
Uchiyama et. al., "Ultrafine flexible spinal endoscope (myeloscope) and discovery of an unreported subarachnoid lesion," *Spine*, 23(21):2358-2362, 1998.
U.S. Pat. No. 5,085,631.
U.S. Pat. No. 5,470,318.

What is claimed is:

1. A method of achieving intracranial access from an entry location in spinal subarachnoid space, comprising:
   introducing a guidewire into the spinal subarachnoid space;
   introducing a device over the guidewire and into the spinal subarachnoid space;
   advancing the device from the spinal subarachnoid space into the intracranial subarachnoid space;
   introducing a penetration apparatus through the device;
   puncturing pia mater within the intracranial space using the penetration apparatus;
   advancing an electrode through the device and through the pia mater; and placing the electrode on or in brain tissue.

2. The method of claim 1, further comprising:
   applying electric current to the brain tissue with the electrode.

3. The method of claim 2, where the electrode is linked to a wire through which a signal can be sent to the electrode to cause application of the electric current.

4. The method of claim 2, where a signal is wirelessly sent to the electrode to cause application of the electric current.

5. The method of claim 1, further comprising:
   applying heat to the brain tissue with the electrode.

6. The method of claim 5, where the electrode is linked to a wire through a signal can be sent to the electrode to cause application of the heat.

7. The method of claim 5, where a signal is wireless sent to the electrode to cause application of the heat.

8. The method of claim 1, further comprising:
   applying cryothermal stimulation to the brain tissue with the electrode.

9. The method of claim 8, where the electrode is linked to a wire through a signal can be sent to the electrode to cause the cryothermal stimulation.

10. The method of claim 8, where a signal is wireless sent to the electrode to cause the cryothermal stimulation.

11. The method of claim 1, where the penetration apparatus includes an outer sleeve element and an inner puncture element, and the outer sleeve element and the inner puncture element are slidably coupled together.

12. The method of claim 11, further comprising:
   applying electric current to the brain tissue with the electrode.

13. The method of claim 12, where the electrode is linked to a wire through which a signal can be sent to the electrode to cause application of the electric current.

14. The method of claim 12, where a signal is wirelessly sent to the electrode to cause application of the electric current.

15. The method of claim 11, further comprising:
   applying heat to the brain tissue with the electrode.

16. The method of claim 15, where the electrode is linked to a wire through a signal can be sent to the electrode to cause application of the heat.

17. The method of claim 15, where a signal is wireless sent to the electrode to cause application of the heat.

18. The method of claim 11, further comprising:
   applying cryothermal stimulation to the brain tissue with the electrode.

19. The method of claim 18, where the electrode is linked to a wire through a signal can be sent to the electrode to cause the cryothermal stimulation.

20. The method of claim 18, where a signal is wireless sent to the electrode to cause the cryothermal stimulation.

* * * * *

UNITED STATES PATENT AND TRADEMARK OFFICE
CERTIFICATE OF CORRECTION

PATENT NO.         : 7,787,954 B2
APPLICATION NO.    : 12/323204
DATED              : August 31, 2010
INVENTOR(S)        : Phillip D. Purdy Page 1 of 1

It is certified that error appears in the above-identified patent and that said Letters Patent is hereby corrected as shown below:

Title page, item (54) Title, line 2, and in column 1, line 2, delete "SUBARACNHNOID" and insert --SUBARACHNOID-- therefor.

In claim 1, column 31, line 57, delete "in spinal" and insert --in the spinal-- therefor.

In claim 1, column 31, line 60, delete "guidewire and into" and insert --guidewire into-- therefor.

In claim 1, column 32, line 2, delete "into the intracranial" and insert --into an intracranial-- therefor.

Signed and Sealed this
Twenty-first Day of June, 2011

David J. Kappos
*Director of the United States Patent and Trademark Office*